United States Patent
Sugiyama et al.

(10) Patent No.: US 6,495,636 B2
(45) Date of Patent: Dec. 17, 2002

(54) OXETANE COMPOUND, OXETANE COPOLYMER, AND PROCESS FOR PRODUCING THE OXETANE COMPOUND

(75) Inventors: Naoki Sugiyama, Tokyo (JP); Manabu Sekiguchi, Tokyo (JP); Hozumi Sato, Tokyo (JP)

(73) Assignee: JSR Corporation, Tokyo (JP)

( * ) Notice: Subject to any disclaimer, the term of this patent is extended or adjusted under 35 U.S.C. 154(b) by 143 days.

(21) Appl. No.: 09/756,220

(22) Filed: Jan. 9, 2001

(65) Prior Publication Data

US 2001/0002423 A1 May 31, 2001

Related U.S. Application Data

(63) Continuation of application No. PCT/JP99/03432, filed on Jun. 25, 1999.

(30) Foreign Application Priority Data

Jul. 9, 1998 (JP) ............................. 10-194815
Jul. 9, 1998 (JP) ............................. 10-194816

(51) Int. Cl.$^7$ ........................ C08G 59/38; C08F 214/28; C07D 305/06
(52) U.S. Cl. ..................... 525/326.3; 528/111; 549/510
(58) Field of Search ............................ 549/50; 528/111; 525/326.3

(56) References Cited

U.S. PATENT DOCUMENTS 6,284,898 B1 * 9/2001 Moszner et al. ............ 549/214
6,417,314 B1 * 7/2002 Malik et al. ................. 528/60

FOREIGN PATENT DOCUMENTS

| JP | 7-17958 | 1/1995 |
| JP | 10-316670 | 12/1998 |
| JP | WO00/02873 | 1/2000 |

* cited by examiner

Primary Examiner—Deborah C. Lambkin
(74) Attorney, Agent, or Firm—Oblon, Spivak, McClelland, Maier & Neustadt, P.C.

(57) ABSTRACT

Oxetane compounds represented by general formula (1), which are excellent in radical polymerizability and cationic polymerizability and in compatibility and copolymerizability with other copolymerizable monomers; a process for producing the compounds; and an oxetane copolymer which is excellent in compatibility among the monomer units and has a low water absorption and excellent transparency.

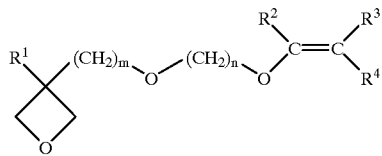

(1)

[In general formula (1), substituent $R^1$ is hydrogen, alkyl, fluorine, fluoroalkyl, allyl, aryl, furyl, or thienyl; substituents $R^2$, $R^3$, and $R^4$ each independently is hydrogen or $C_{1-6}$ alkyl; and m and n each is an integer of 1 to 10 (provided that not all of $R^2$, $R^3$, and $R^4$ are hydrogen)].

30 Claims, 8 Drawing Sheets

OXETANE COMPOUND, OXETANE COPOLYMER, AND PROCESS FOR PRODUCING THE OXETANE COMPOUND

CROSS REFERENCE TO RELATED APPLICATION

This is a continuation application of PCT International Application of PCT/JP99/03432 filed on Jun. 25, 1999.

BACKGROUND OF THE INVENTION

1. Field of the Invention

The present invention relates to an oxetane compound, a process for producing the same, and an oxetane copolymer. More specifically, the present invention relates to an oxetane compound which has an excellent property in radical polymerization, cationic polymerization, compatibility and copolymerization-ability with other unsaturated monomers (vinyl monomers or the like); a process for producing such an oxetane compound effectively; and an oxetane copolymer containing a fluorine component as a copolymerization component.

2. Description of the Background

Epoxy resins have been widely used as a photocuring component in photocuring compositions since they are excellent in heat resistance, adhesion to various substrates and cationic polymerization.

However, reaction of a photocuring composition using a conventional epoxy resin is not easily controlled in the presence of an acid or alkali. The composition reacts even at room temperature. Problems that preservation stability and convenience are poor arise.

For this reason, suggestions as follows are made on: a photocuring component and a photocuring catalyst are physically divided in a photocuring composition using an epoxy resin so as to prepare a so-called two-liquid type adhesive. However, before use, the photocuring component and the photocuring catalyst must be homogeneously mixed. Thus, convenience thereof is poor and bad photocuring is caused because of insufficient mixing.

Thus, as cationic polymerizable resins instead of epoxy resins, oxetane compounds are suggested. For example, JP-A-6-16804, JP-A-7-53711, JP-A-7-62082, JP-A-9-31186, JP-A-7-173279 and JP-A-9-143259 disclose photocuring oxetane compositions containing as a main component an oxetane compound which does not contain ether bonds other than any oxetane group (active energy beam curing compositions).

Furthermore, JP-A-7-17958 discloses an oxetane compound represented by the following general formula (6); an ultraviolet ray curing composition comprising the oxetane compound and a cationic photopolymerization initiator; and a process for producing an oxetane compound, using a synthesis process by Pattison (Pattison, J. Am. Chem. Soc., 1958, 79).

(6)

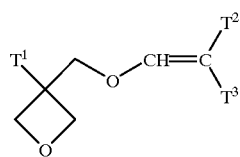

wherein $T^1$ represents hydrogen, alkyl having 1 to 6 carbon atoms, fluorine, fluoroalkyl having 1 to 6 carbon atoms, ally, aryl, furyl or thienyl, $T^2$ represents alkyl having 1 to 6 carbon, and $T^3$ represents hydrogen or alkyl having 1 to 6 carbon atoms.

However, the oxetane compound represented by the general formula (6) has insufficient radical polymerization-ability. Thus, there arise problems that the oxetane compound has poor copolymerization-ability with other unsaturated monomers, in particular fluorinated monomers. According to the synthesis process by Pattison used to synthesize the oxetane compound represented by the general formula (6), it is impossible to synthesize any oxetane compound containing in the molecule thereof plural ether bonds other than any oxetane group.

Thus, the inventors of the present invention made investigations eagerly. As a result, the inventors have found that the above-mentioned problems can be solved by causing plural ether bonds other than any oxetane group to be contained in the molecule of an oxetane compound.

The inventors have found that plural ether bonds other than any oxetane group contained in the molecule could improve remarkably the radical polymerization-ability of unsaturated groups in the oxetane compound while the cationic polymerization-ability of the oxetane group is maintained.

The inventors have also found that by causing plural ether bonds other than any oxetane group to be contained in the molecule, the compatibility with other copolymerizable monomers and radical polymerization-ability are improved so that copolymers having uniform properties can be obtained.

Thus, an object of the present invention is to provide an oxetane compound excellent in radical polymerization-ability and cationic polymerization-ability and in copolymerization-ability; and an oxetane copolymer obtained from such an oxetane compound.

Another object of the present invention is to provide a process for producing an oxetane compound effectively.

DISCLOSURE OF THE INVENTION

The present invention is an oxetane compound which contains in the molecule thereof plural ether bonds other than any oxetane group and is represented by the general formula (1):

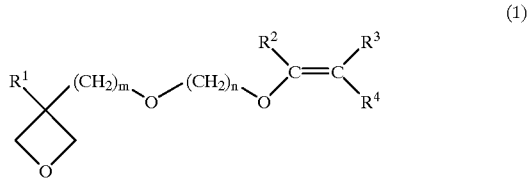

wherein substituent $R^1$ is hydrogen, alkyl, fluorine, fluoroalkyl, ally, aryl, furyl or thienyl; substituents $R^2$, $R^3$ and $R^4$ each independently is hydrogen or alkyl having 1 to 6 carbon atoms; and m and n each is an integer of 1 to 10 (excluding a compound where in all of substituents $R^2$, $R^3$ and $R^4$ are not hydrogen).

The oxetane compound having the above-mentioned structure is excellent in radical polymerization-ability and cationic polymerization-ability and in compatibility with other copolymerizable monomers.

Another aspect of the present invention is an oxetane copolymer obtained by radical polymerizing an oxetane compound represented by the general formula (1) (including a compound wherein all of the substituents $R^2$, $R^3$ and $R^4$ are hydrogen), its number average molecular weight converted to polystyrene, which is measured by GPC, being in the range of 1,000 to 1,000,000.

For example, the oxetane copolymer is represented by the general formula (2):

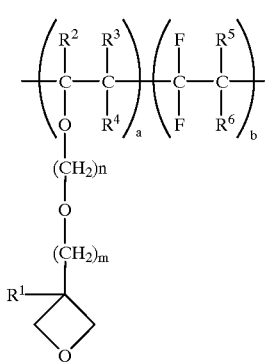

(2)

wherein substituent $R^1$ is hydrogen, alkyl, fluorine, fluoroalkyl, ally, aryl, furyl or thienyl; substituents $R^2$, $R^3$ and $R^4$ each independently is hydrogen or alkyl having 1 to 6 carbon atoms; $R^5$ is hydrogen, fluorine or chlorine; $R^6$ is hydrogen, fluorine, fluoroalkyl, alkoxy or fluorinated alkoxy; m and n each is an integer of 1 to 10; a and b each is in the range of 0.1 to 99.9% by mole(a+b=100 mol %).

Note that both ends of the main chain of the general formula (2)(both ends are not described in the general formula (2)) are hydrogen, groups composed of a part of a radical polymerization initiator, or the like.

The oxetane copolymer having the above-mentioned structure is excellent in compatibility with a fluorine compound as a copolymerization component and in water repellence and transparency, and has a low water absorption property. Also, such oxetane copolymer has a good photocuring property.

A further aspect of the present invention is a process for producing an oxetane compound represented by the general formula (1), characterized by reacting an oxetane alcohol compound represented by the following general formula (4) with a halogenated vinyl ether compound represented by the following general formula (5) in the presence of a phase transfer catalyst:

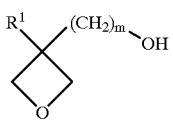

(4)

wherein substituent $R^1$ and repetition number m are the same in the general formula (1),

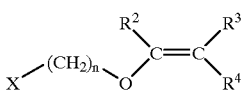

(5)

wherein substituents $R^2$, $R^3$ and $R^4$ and repetition number n each is the same in the general formula (1), and X is a halogen atom.

By such process for producing an oxetane compound, it is possible to produce effectively an oxetane compound excellent in both of radical polymerization-ability and cationic polymerization-ability and in compatibility with other copolymerizable monomers.

BEST MODES FOR CARRYING OUT THE INVENTION

Figure 1:
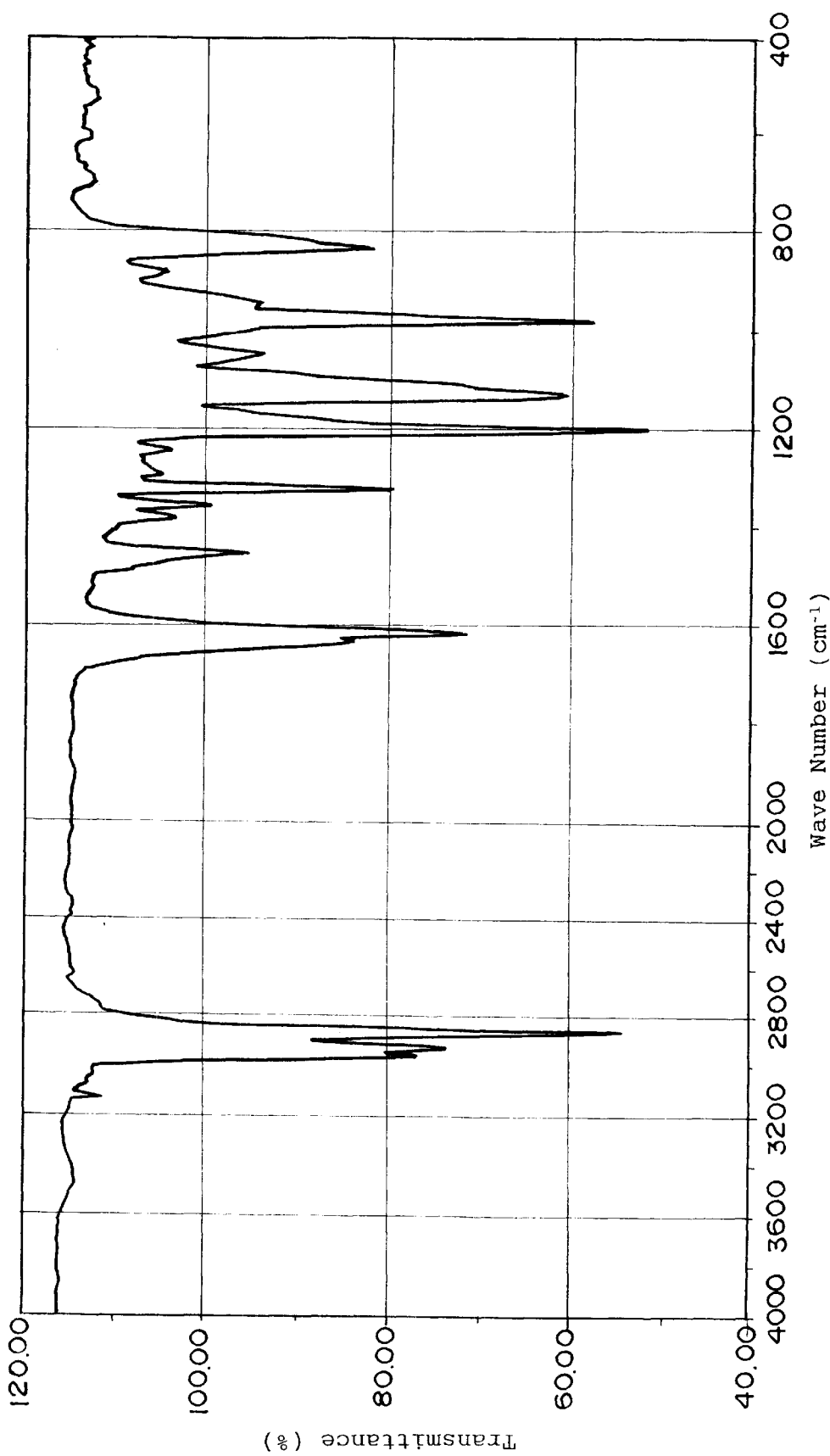
FIG. 1 is an infrared absorption spectrum of 2-(3-methyl-3-oxetanemethoxy)ethyl vinyl ether.

Embodiments of the present invention will be specifically described from the viewpoints of a process for producing an oxetane compound, an oxetane copolymer and a use example of the oxetane copolymer (a photocuring composition).

[First Embodiment]

The first embodiment of the present invention is a process for producing an oxetane compound which contains in the molecule thereof plural ether bonds other than any oxetane group and is represented by the general formula (1).

(1) Raw Materials

First, raw materials of an oxetane compound represented by the general formula (1) will be described.

That is, any raw material can be used if the raw material makes it possible to produce an oxetane compound according to the method by Motoi (Motoi et. al., Bull. Chem. Soc. Jpn. 61, 1998). Specifically, an oxetane compound represented by the general formula (1) can be produced by etherification-reacting an oxetane alcohol compound represented by the general formula (4) with a halogenated vinyl ether compound represented by the general formula (5).

More specific oxetane compound(s) represented by the general formula (4) may be one or a combination of two or more selected from 3-methyl-3-oxetane methanol, 3-methyl-3-oxetane ethanol, 3-methyl-3-oxetane propanol, 3-ethyl-3-oxetane methanol, 3-ethyl-3-oxetane ethanol, 3-ethyl-3-oxetane propanol, 3-propyl-3-oxetane methanol, 3-propyl-3-oxetane ethanol, 3-propyl-3-oxetane propanol or the like.

More specific halogenated vinyl ether compound(s) represented by the general formula (5) may be one or a combination of two or more selected from 2-chloroethyl vinyl ether, 2-bromoethyl vinyl ether, 3-chloropropyl vinyl ether, 3-bromopropyl vinyl ether, 4-chlorobutyl vinyl ether, 4-bromobutyl vinyl ether, or the like.

The reaction ratio between the oxetane alcohol compound represented by the general formula (4) and the halogenated vinyl ether compound represented by the general formula (5)

is not particularly limited. Preferably, 0.1–10 moles of the halogenated vinyl ether compound represented by the general formula (5) is reacted with 1 mole of the oxetane alcohol compound represented by the general formula (4). If the ratio of the halogenated vinyl ether compound is out of this range, a great deal of unreacted monomers remain so that the radical reactivity of the oxetane compound occasionally decreases.

More preferably, therefore, 0.3 to 3.0 moles of the halogenated vinyl ether compound represented by the general formula (5) is reacted with 1 mole of the oxetane alcohol compound represented by the general formula (4).

(2) Reaction Temperature

The following will describe the reaction temperature upon the production of the oxetane compound represented by the general formula (1). This reaction temperature is decided, considering the yield of the oxetane compound or the like. For example, a temperature in the range of 0 to 100° C. is preferable.

The reasons therefor are as follows. If the reaction temperature is below 0° C., the reactivity of the raw materials occasionally decrease remarkably so that the yield may also decrease remarkably. On the other hand, if the reaction temperature is over 100° C., the kind of the organic solvent that can be used may be limited.

Accordingly, the reaction temperature upon the production of the oxetane compound is more preferably in the range of 10 to 90° C. and still more preferably in the range of 20 to 80° C.

(3) Reaction Time

The following will describe the reaction time upon the production of the oxetane compound represented by the general formula (1). This reaction temperature is decided, considering the yield of the oxetane compound, the reaction time or the like. For example, a value in the range of 10 minutes to 100 hours is preferable at a reaction temperature of 0 to 100° C. The reasons therefor are as follows. If the reaction time is below 10 minutes, a great deal of unreacted raw materials occasionally remain. On the other hand, if the reaction time is over 100 hours, the productivity occasionally decreases. Accordingly, the reaction time upon the production of the oxetane compound is more preferably set up to a value in the range of 30 minutes to 50 hours and still more preferably set up to a value in the range of 1 to 10 hours.

(4) Reaction Atmosphere (pH)

The following will describe the reaction atmosphere (pH) upon the production of the oxetane compound represented by the general formula (1). This reaction atmosphere is decided, considering the yield of the oxetane compound or the like. For example, a value in the range of 5 to 14 is preferable. The reasons therefor are as follows. If the pH value is below 5, side reactions are easily generated so that the yield may occasionally decrease. On the other hand, if the pH value is over 14, the kinds of the raw materials for use may be excessively limited.

Accordingly, the pH value upon the production of the oxetane compound is more preferably set up to a value in the range of 6 to 14 and still more preferably set up to a value in the range of 7 to 14.

(5) Phase Transfer Catalyst

The following will describe the phase transfer catalyst used upon the production of the oxetane compound represented by the general formula (1).

This phase transfer catalyst is added to improve the reactivity of the oxetane alcohol compound and the halogenated vinyl ether compound. For example, the added amount of the phase transfer catalyst is preferably set up to a value in the range of 0.1 to 30 parts by weight per 100 parts by weight of the total of the raw materials. The reasons therefor are as follows. If the add amount of the phase transfer catalyst is below 0.1 part by weight, the reactivity of the raw materials with each other decreases remarkably so that the yield correspondingly decreases remarkably. On the other hand, if the added amount of the phase transfer catalyst is over 30 parts by weight, purification occasionally becomes difficult. Accordingly, the added amount of the phase transfer catalyst upon the production of the oxetane compound is more preferably set up to a value in the range of 1 to 20 parts by weight and still more preferably set up to a value in the range of 2 to 10 parts by weight per 100 parts by weight of the total of the raw materials.

The kind of the phase transfer catalyst is not particularly limited. For example, the phase transfer catalyst is preferably both of a quaternary ammonium salt and a quaternary phosphonium salt, or either thereof.

(6) Organic Solvent

Upon the production of the oxetane compound represented by the general formula (1), an organic solvent is preferably used. This organic solvent is preferably a liquid whose boiling point under the atmosperic pressure is 250° C. or lower since the liquid is a good solvent for the raw materials and the production can be made easy.

(7) Example of the Structure of the Oxetane Compound

On the basis of an infrared absorption spectrum shown in FIG. 1 and a proton-NMR spectrum shown in FIG. 2, an example of the oxetane compound represented by the general formula (1) will be described.

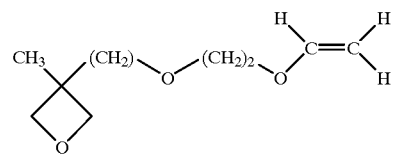

(7)

The infrared absorption spectrum shown in FIG. 1 is related to 2-(3-methyl-3-oxetanemethoxy)ethyl vinyl ether represented by the general formula (7) (Example 1), and was measured using a Fourier type infrared spectrometer JIR-5500 (made by JEOL Ltd.). As its horizontal axis, wavenumbers (cm$^{-1}$) are adopted and represented. As its vertical axis, infrared absorption ratios (%) are adopted and represented.

As can be understood from the infrared absorption spectrum shown in FIG. 1, a remarkable peak assigned to vibration of the oxetane ring appears at a wavenumber of 977 cm$^{-1}$. A remarkable peak assigned to stretching vibration of the vinyl group also appears at a wavenumber of 1,618 cm$^{-1}$. Furthermore, a peak assigned to the ether bond of the methoxy moiety appears at a wavenumber of 1,128 cm$^{-1}$. Peaks assigned to the ether bond adjacent to the vinyl group appear at wavenumbers of 1,047 cm$^{-1}$ and 1,203 cm$^{-1}$. Thus, if infrared absorption peaks appear at these wavenumbers, it can be acknowledged that there are an oxetane ring, a vinyl group and ether bonds.

Figure 2:
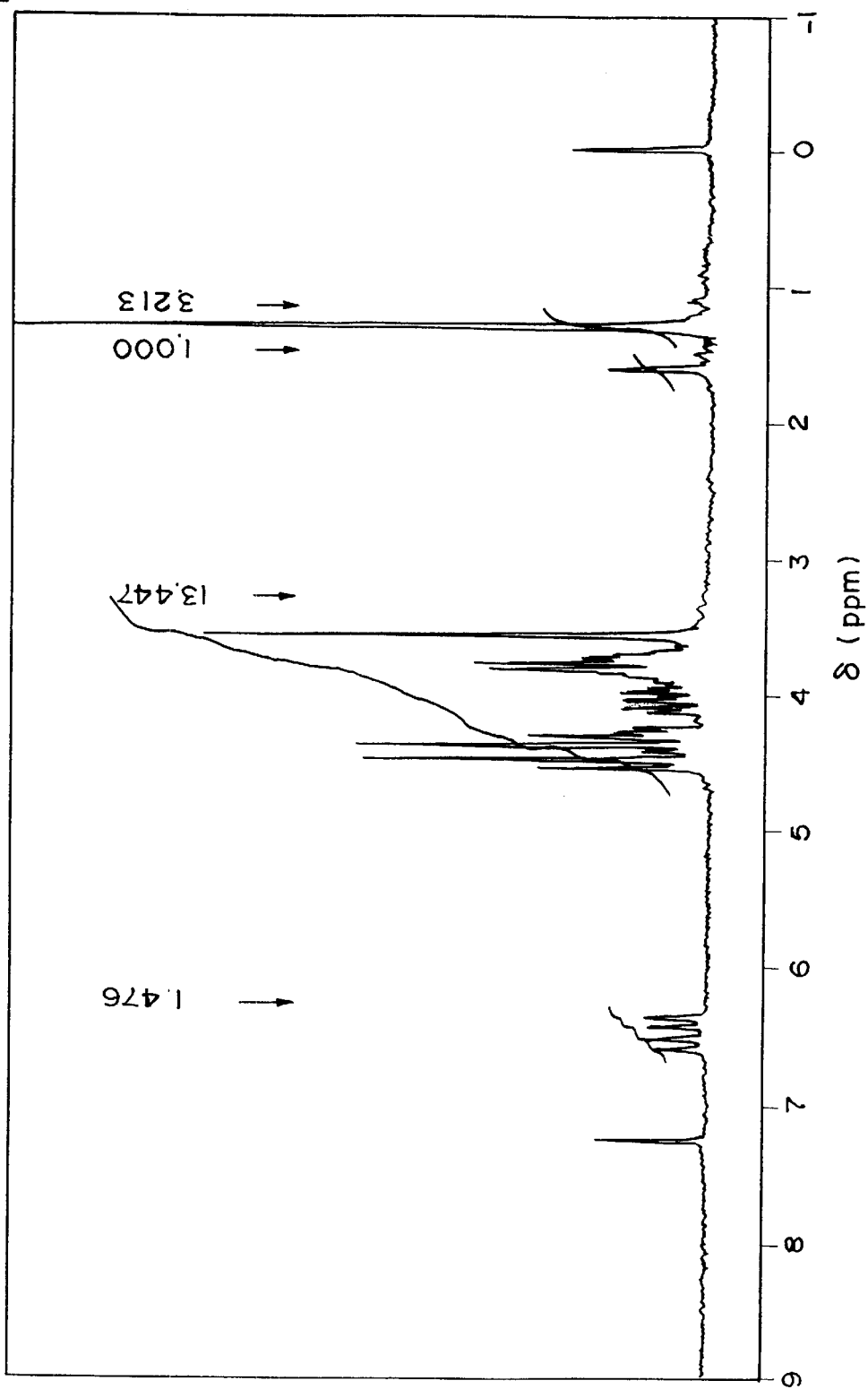
FIG. 2 is a proton-NMR spectrum of 2-(3-methyl-3-oxetanemethoxy)ethyl vinyl ether.

The proton-NMR spectrum shown in FIG. 2 is related to 2-(3-methyl-3-oxetanemethoxy)ethyl vinyl ether (Example 1), and was measured using a proton-NMR measuring machine JNM-EX90 (made by JEOL Ltd.) under conditions that a solvent was CDCl$_3$ and resolution power was 90 MHz. As its horizontal axis, δ (ppm) are adopted and represented. As its vertical axis, hydrogen intensities are adopted and represented.

Data thereon will be described in Example 1. Briefly, in the proton-NMR spectrum, main peaks assigned to hydrogen atoms that 2-(3-methyl-3-oxetanemethoxy)ethyl vinyl ether has appear at δ values of 1.3, 3.5, 3.7, 3.9, 4.0–4.2, 4.3–4.5 and 6.5.

(8) Substituents in the Oxetane Compound Represented by the General Formula (1)

The substituent $R^1$ in the oxetane compound based on the general formula (1) is hydrogen, alkyl, fluorine, fluoroalkyl, ally, aryl, furyl or thienyl, as described above.

From the viewpoint of excellent radical reactivity of the unsaturated group and excellent cationic polymerization-ability of the oxetane ring, the substituent $R^1$ is preferably alkyl having 1–4 carbon atoms, and more preferably methyl or ethyl.

The substituents $R^2$, $R^3$ and $R^4$ in the general formula (1) each independently is preferably hydrogen or alkyl having 1–6 carbon atoms, and is more preferably hydrogen. This is because in the case that the substituents $R^2$, $R^3$ and $R^4$ are all hydrogen, the radical reaction rate of the oxetane compound is particularly high. The substituents $R^2$, $R^3$ and $R^4$ may be the same or different.

The repetition number m in the general formula (1) is an integer of 1 to 10. From the viewpoint that the radical reactivity of the vinyl group is better and the reaction of the raw materials with each other upon the production of the oxetane compound is easily caused, the repetition number m is more preferably an integer of 1 to 4.

The repetition number n in the general formula (1) is also an integer of 1 to 10. From the viewpoint that the radical reactivity of the vinyl group is better and the reaction of the raw materials with each other upon the production of the oxetane compound is easily caused, the repetition number n is more preferably an integer of 2 to 5.

(9) Copolymerizable Monomers

The compound represented by the general formula (1) has a characteristic that it is excellent in compatibility and copolymerization-ability with other copolymerizable monomers. Therefore, the oxetane compound together with one or more of various copolymerizable monomers can be made to a homogeneous copolymer. Preferable copolymerizable monomers that can be used together may be an ethylenic unsaturated monomer (other than fluorine-containing unsaturated monomers) and a fluorine-containing unsaturated monomer (which may be referred to as a fluorine compound hereinafter). These copolymerizable monomers will be described in detail as another embodiment.

[Second Embodiment]

The second embodiment relates to an oxetane copolymer represented by the general formula (2) and obtained by radical polymerizing an oxetane compound represented by the general formula (1) and a fluorine compound represented by the general formula (3) as copolymerizable components.

In the second embodiment, the oxetane compound, the process for producing the oxetane compounds, or the like described about the first embodiment are also used as they are. Thus, the description thereon is omitted herein.

(1) Fluorine Compound
i) Kind

The fluorine compound represented by the general formula (3) may be a first group fluorine compound or a second group fluorine compound as described below. By using not only the first group fluorine compound but also the second group fluorine compound, the fluorine content in the oxetane copolymer can be effectively made high.

As such a first group fluorine compound, there is preferably used tetrafluoroethylene, hexafluoropropylene, 3,3,3-trifluoropropylene, chlorotrifluoroethylene, fluorinated vinylidene or the like. These first fluorine compounds may be used alone or in combination of two or more.

Examples of the second group fluorine compound include alkyl perfluorovinyl ethers or alkoxyalkyl perfluorovinyl ethers; perfluoro(alkyl vinyl ethers) such as perfluoro (methyl vinyl ehter), perfluoro(ethyl vinyl ether), perfluoro (propyl vinyl ether), perfluoro(butylvinyl ether) and perfluoro(isobutylvinyl ether); and perfluoro(alkoxyalkyl vinyl ehters) such as perfluoro(propoxypropyl vinyl ehter).

ii) Added Amount of the Fluorine Compound

The amount of the fluorine compound added to the oxetane compound is not particularly limited. For example, the amount is preferably set up to a value in the range of 0.1 to 2,000 parts by weight per 100 parts by weight of the oxetane compound. The reasons therefor are as follows. If the added amount of the fluorine compound is below 0.1 part by weight, advantages based on the addition may be exhibited. On the other hand, if the added amount is over 2,000 parts by weight, homogenous mixing becomes difficult or photocuring ability tends to deteriorate.

Therefore, the added amount of the fluorine compound is more preferably set up to a value in the range of 1 to 1,000 parts by weight, and more preferably set up to a value in the range of 5 to 500 parts by weight.

(2) Copolymerizable Components (Copolymerization Monomers)

In the second embodiment, as one or more of other copolymerizable components, compound(s) described below are preferably added. Use of nonionic reactive emulsifiers, unsaturated monomers having a hydrolyzable silyl group, unsaturated monomers having an epoxy group, and unsaturated monomers having a hydroxyl group will be described in detail in other embodiments. Therefore, the copolymerizable components herein mean compounds other than the nonionic reactive emulsifiers or the like.

Such a copolymerizable component may be an ethylenic unsaturated monomer. The ethylenic unsaturated monomer is a compound containing in the molecule thereof an ethylenic unsaturated bond (C=C), and can be defined as i) a monofunctional monomer having in the molecule thereof one ethylenic unsaturated bond, and ii) a polyfunctional monomer having in the molecule thereof two or more ethylenic unsaturated bonds.

i) Monofunctional Monomer

Therefore, the above-mentioned monofunctional monomer having an ethylenic unsaturated bond is preferably, for example, isobornyl (meth)acrylate, lauryl (meth)acrylate, butoxyethyl (meth)acrylate, polyethylene glycol mono (meth)acrylate, bornyl (meth)acrylate, or methyltriethylene diglycol (meth)acrylate since no aromatic ring is contained to keep weather resistance.

Since the yield (monomer conversion rate) in polymerization of the copolymer can be made higher, preferable are alkyl vinyl ethers, cycloalkyl vinyl ethers and vinyl esters of carbonic acids.

Since the fluorine content in the copolymer can be very minutely adjusted, preferable are low molecular weight monomers such as methyl vinyl ether, ethyl vinyl ether, propyl vinyl ether, isopropyl vinyl ether, vinyl acetate, vinyl propionate, vinyl butyrate and vinyl pivalate, or 2,2,2-trifluoroethyl (meth)acrylate, 2,2,3,3-tetrafluoropropyl (meth)acrylate, 2,2,3,3,3-pentafluoropropyl (meth)acrylate, 2-(perfluorobutyl)ethyl (meth)acrylate, 2-(perfluorohexyl) ethyl (meth)acrylate, and 2-(perfluorooctyl)ethyl (meth) acrylate.

Furthermore, there is preferably used a branched monomer such as isopropyl vinyl ether, tert-butyl vinyl ether or vinyl pivalate since the fluorine content can be made higher without a decrease in hardness of the oxetane copolymer.

ii) Polyfunctional Monomer

The above-mentioned polyfunctional monomer having ethylenic unsaturated bonds is preferably an acrylate having no aromatic ring since its weather resistance and heat resistance are better. Examples thereof include ethylene glycol di(meth)acrylate, dicylocopentenyl di (meth)acrylate, triethylene glycol diacrylate, tetraethylene glycol di(meth)acrylate, tricyclodecanediyldimethylene di(meth)acrylate, trimethylolpropane tri(meth)acrylate, dipentaerythritol hexa (meth)acrylate, dipentaerythiritol penta(meth)acrylate, and dipentaerythritol tetra(meth)acrylate.

iii) Added Amount of the Copolymerizable Component

The amount of the copolymerizable component (copolymerization monomer) added to the oxetane compound is not particularly limited. For example, the amount is preferably set up to a value in the range of 0.1 to 2000 parts by weight per 100 parts by weight of the oxetane compound. The reasons therefor are as follows. If the added amount of the copolymerizable component is below 0.1 part by weight, advantages based on the addition may be exhibited. On the other hand, if the added amount is over 2,000 parts by weight, homogenous mixing occasionally becomes difficult or photocuring ability occasionally deteriorate.

Therefore, the added amount of the copolymerizable component is more preferably set up to a value in the range of 1.0 to 2,000 parts by weight, and more preferably set up to a value in the range of 2.0 to 1,000 parts by weight.

(3) Production Process

The oxetane copolymer as the second embodiment can be obtained by adding a radical generator to the copolymerizable components and performing radical polymerization by heating or radiation of light.

As the radical generator, a radical photo-polymerization initiator, a radical thermal polymerization initiator or the like can be used. The radical polymerization initiator is a compound that is decomposed and generates radicals by receiving energy rays such as light, or that generates radicals by being heated at a decomposition temperature or higher.

It is preferred that as an especial radical generator, a polysiloxane compound containing an azo group is used. The polysiloxane containing an azo group is one kind of radical thermal polymerization initiators and is a compound wherein the azo group generates radicals by being heated at a decomposition temperature or higher. Moreover, the polysiloxane is a compound having a siloxane structure in the molecule thereof, and is, for example, a compound represented by the general formula (8). This compound is a polymer material whose number average molecular weight is in the range of 10,000 to 100,000.

(8)

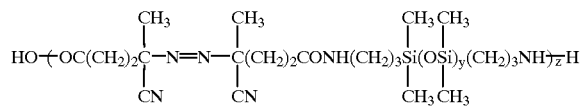

wherein y and z are repetition numbers, y is an integer of 1 to 200 and z is an integer of 5 to 10.

By using as the radical generator such polysiloxane containing an azo group, it is possible to radical-copolymerize the copolymerization components and introduce siloxane segments (structures) easily to the oxetane copolymer. Therefore, it is possible to give lubricity and abrasion resistance to the oxetane copolymer.

The radical generator is preferably used in the manner that the amount of the radical generator is decided so that the amount of the siloxane segments in the oxetane copolymer is a value in the range of 0.1 to 20% by mole. If the amount of the siloxane segments is below 0.1% by mole, advantages based on the introduction tends not to be exhibited. On the other hand, if the amount is over 20% by mole, the transparency of the oxetane copolymer tends to deteriorate.

Therefore, the amount of the radical generator is decided in the manner that the amount of the siloxane segments is more preferably a value in the range of 0.1 to 15% by mole and is still more preferably a value in the range of 0.1 to 10% by mole.

The added amount of the radical generator is not particularly limited. For example, the added amount is preferably set up to a value in the range of 0.01 to 10 parts by weight per 100 parts by weight of the total of the oxetane compound and the fluorine compound. If the added amount of the radical generator is below 0.01 part by weight, the remaining amount of unreacted monomers tends to be large. On the other hand, if the added amount is over 10 parts by weight, the molecular weight decreases extremely or the heat resistance of the resultant oxetane copolymer tends to decrease. Accordingly, the added amount of the radical generator is more preferably set up to a value in the range of 0.1 to 5 parts by weight.

The method of the radical polymerization used in the second embodiment is not particularly limited, and may be an emulsion polymerization, suspension polymerization, bulk polymerization, solution polymerization or the like. Solution polymerization, which is more typical radical polymerization, will be specifically described herein.

In order to perform solution polymerization, it is necessary to use an organic solvent. This organic solvent can be selected from the scope that does not damage the objects and effects of the present invention. Usually, preferable is an organic compound having a boiling point, under the atmosperic pressure, of 50 to 200° C. and causing the respective constituents to be homogeneously dissolved.

Conditions for the solution polymerization are not particularly limited. For example, the solution is preferably heated within the temperature range of 50 to 200° C. for 10 minutes to 30 hours while the above-mentioned organic solvent is subjected to reflux.

Preferably, an inert gas purge is performed not only during the solution polymerization but also before the solution polymerization in order that no generated radicals are inactivated. As the inert gas, nitrogen gas is suitably used.

(4) Number Average Molecular Weight of the Oxetane Copolymer

The number average molecular weight of the oxetane polymer is not particularly limited. For example, the number average molecular weight converted to polystyrene, measured by GPC, is preferably a value in the range of 1,000 to 1,000,000. The reasons therefor are as follows. If the number average molecular weight is below 1,000, the heat resistance of the oxetane copolymer occasionally decreases. On the other hand, the number average molecular weight is over 1,000,000, the viscosity occasionally rises so that handling may become difficult.

Accordingly, the number average molecular weight of the oxetane copolymer is preferably set up to a value in the range of 5,000 to 500,000, and more preferably set up to a value in the range of 10,000 to 100,000.

(5) The Amount of Fluorine in the Oxetane Copolymer

The amount of fluorine in the oxetane copolymer is not particularly limited. For example, the amount of fluorine (converted to the weight of fluorine atoms) is preferably set up to a value in the range of 10 to 80% by weight per the total 10% by weight of the oxetane copolymer. If the amount of fluorine is below 10% by weight, the heat resistance and the water repellence of the oxetane copolymer occasionally decreases. On the other hand, the amount of fluorine is over 80% by weight, the oxetane compound is occasionally relatively reduced so that photocuring ability may decrease or the compatibility between the oxetane compound and the fluorinated compound may decrease.

Accordingly, the amount of fluorine (converted to the weight of fluorine atoms) in the oxetane copolymer is more preferably set up to a value in the range of 20 to 70% by weight, and still more preferably set up to a value in the range of 30 to 70% by weight.

(6) Water Absorption of the Oxetane Copolymer

The water absorption of the oxetane copolymer is not particularly limited. For example, the water absorption is preferably a value in the range of 0.1 to 10% by weight. The reasons are as follows. If the water absorption is below 0.1% by weight, the kinds of the copolymerizable components for use are occasionally limited. On the other hand, if the water absorption is over 10% by weight, the creep resistance and heat resistance of the oxetane copolymer occasionally decreases.

Accordingly, the water absorption of the oxetane copolymer is more preferably set up to a value in the range of 0.1 to 7% by weight, and still more preferably set up to a value in the range of 0.1 to 5% by weight.

(7) Water Repellence

The water repellence of the oxetane copolymer can be represented as the contact angle with water. For example, the value of the contact angle is preferably from 60 to 120°. The reasons are as follows. If the contact angle is below 60°, absorption of water is occasionally caused easily. On the other hand, if the contact angle is over 120°, the kinds of the copolymerizable components for use are occasionally limited.

Accordingly, the contact angle of the oxetane copolymer is more preferably set up to a value in the range of 70 to 120°, and still more preferably set up to a value in the range of 80 to 120°.

(8) Transparency of the Oxetane Copolymer

The transparency of the oxetane copolymer is not particularly limited. For example, the light transmittance of light in the range of visible ray wavelengths is preferably a value in the range of 50% or more. The reasons therefor are as follows. If the light transmittance is below 50%, the transparency is occasionally lowered so that uses may be limited. Accordingly, the light transmittance in the oxetane copolymer is more preferably set up to 85% or more and still more preferably set up to 95% or more.

(9) Form of the Oxetane Copolymer

The form of the oxetane copolymer which is the second embodiment is not particularly limited. It is preferred that, for example, by adding an organic solvent, the oxetane copolymer can be made into a liquid form (an oxetane copolymer solution). By preparing the oxetane copolymer solution, convenience becomes good and a film having a uniform film thickness can be formed on a substrate or the like.

(10) Additives

If necessary, one or more of various additives may be contained in the oxetane copolymer which is the second embodiment. Examples of such additives include polymers or oligomers such as acrylic resins, epoxy resins, polyamides, polyamideimides, polyurethanes, polybutadiene, polychloroprene, polyethers, polyesters, styrene/butadiene block copolymers, pertoreum resins, xylene resins, ketone resins, cellulose resins, fluorine-containing polymers, silicone-based polymers, polysulfide-based polymers.

Examples of preferred additives include polymerization inhibitors such as phenothiazine and 2,6-di-t-butyl-4-methylphenol; a polymerization initiation aid; a leveling agent; a wettability improver; a surfactant; a plasticizer; an ultraviolet ray absorber; an antioxidant; a silane coupling agent; an inorganic filler; a pigment; and compounds such as a dye.

[Third Embodiment]

The third embodiment relates to an oxetane copolymer of the present invention obtained by radical-polymerizing an oxetane compound represented by the general formula (1), a fluorine compound represented by the general formula (3) and a nonionic reactive emulsifier as copolymerizable components. By adding the nonionic reactive emulsifier further as the copolymerizable component as described above, it is possible to obtain an oxetane copolymer having good application ability and leveling ability.

In the third embodiment, the oxetane compound, the fluorine compound, the production process or the like described about the 1st–3rd embodiments are also used in the same way. Thus, the description thereon is omitted herein. That is, the nonionic reactive emulsifier, which is a characteristic in the third embodiment, will be mainly described.

(1) Kind of the Nonionic Reactive Emulsifier

The nonionic reactive emulsifier may be, for example, a compound represented by the general formula (9):

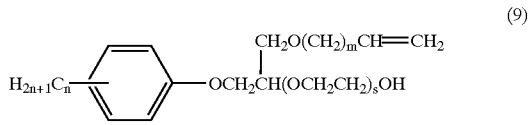

(9)

wherein n is an integer of 1 to 20, m is an integer of 1 to 10, and s is an integer of 1 to 50.

(2) The Added Amount of the Nonionic Reactive Emulsifier

The added amount of the nonionic reactive emulsifier is not particularly limited. For example, the added amount is preferably set up to a value in the range of 0.1 to 200 parts by weight per 100 parts by weight of the oxetane compound represented by the general formula (1). If the added amount of the nonionic reactive emulsifier is below 0.1 part by weight, advantages based on the addition, such as leveling ability, are poorly exhibited. On the other hand, if the added amount is over 200 parts by weight, the photocuring ability occasionally decreases in the case that a photocuring composition is prepared.

Accordingly, the added amount of the nonionic reactive emulsifier is more preferably set up to a value in the range of 0.5 to 100 parts by weight, and still more preferably set up to a value in the range of 0.5 to 50 parts by weight.

[Fourth Embodiment]

The fourth embodiment relates to an oxetane copolymer obtained by radical-polymerizing an oxetane compound represented by the general formula (1), a fluorine compound represented by the general formula (3) and an unsaturated monomer having a hydrolyzable silyl group as copolymerizable(copolymerization) components. By adding the unsaturated monomer having a hydrolyzable silyl group the further as the copolymerization component as described above, it is possible to use the hydrolyzable silyl group as a cation-reactive group. Therefore, photocuring rate can be made high by adding an acid generator to the oxetane copolymer. Moreover, by adding the silyl group, the adhesion to glass or the like can be improved.

In the fourth embodiment, the oxetane compound, the fluorine compound, the production process or the like described about the $1^{st}$ to 3rd embodiments are also used in the same way. Thus, the description thereon is omitted herein. That is, the unsaturated monomer having a hydrolyzable silyl group, which is a characteristic in the third embodiment, will be mainly described.

(1) Kind of the Unsaturated Monomer Having a Hydrolyzable Silyl Group

Examples of this unsaturated monomer having a hydrolyzable silyl group include vinyltrimethoxysilane, vinyltriethoxysilane, vinyltripropoxysilane, vinylmethyldiethoxysilane, vinylethyldimethoxysilane, vinylphenyldimethoxysilane, allyltrimethoxysilane, trimethoxyethyl vinyl ether, and triethoxysilylethyl vinyl ether or the like. These unsaturated monomers having a hydrolyzable silyl group may be used alone or in combination of two or more.

(2) The Added Amount of the Unsaturated Monomer Having a Hydrolyzable Silyl Group The added amount of the unsaturated monomer having a hydrolyzable silyl group is not particularly limited. For example, the added amount is preferably set up to a value in the range of 0.1 to 100 parts by weight per 100 parts by weight of the oxetane compound represented by the general formula (1). If the added amount of the unsaturated monomer having a hydrolyzable silyl group is below 0.1 part by weight, advantages based on the addition, such as adhesion to a glass or the like, tends to be poorly exhibited. On the other hand, if the added amount is over 100 parts by weight, the photocuring ability tends to decrease in the case that a photocuring composition is prepared.

Accordingly, the added amount of the unsaturated monomer having a hydrolyzable silyl group is more preferably set up to a value in the range of 0.5 to 100 parts by weight, and still more preferably set up to a value in the range of 1 to 50 parts by weight.

[Fifth Embodiment]

The fifth embodiment relates to an oxetane copolymer obtained by radical-polymerizing an oxetane compound represented by the general formula (1), a fluorine compound represented by the general formula (3) and an unsaturated monomer having an epoxy group as copolymerizable (copolymerization) components. By adding the unsaturated monomer having an epoxy group the further as the copolymerizable component as described above, it is possible to use the epoxy group as a cation-reactive group. Therefore, photocuring rate can be made high by adding an acid generator to the oxetane copolymer.

In the fifth embodiment, the oxetane compound, the fluorine compound, the production process or the like described about the 1st–4th embodiments are also used in the same way. Thus, the description thereon is omitted herein. That is, the unsaturated monomer having an epoxy group, which is a characteristic in the fifth embodiment, will be mainly described.

(1) Kind of the Unsaturated Monomer Having an Epoxy Group

Examples of this unsaturated monomer having an epoxy group include glycidyl vinyl ether, ally glycidyl ether, glycidyl (meth)acrylate, glycidyl crotonate, and methylglycidyl maleate or the like. These unsaturated monomers having an epoxy group may be used alone or in combination of two or more.

(2) The Added Amount of the Unsaturated Monomer Having an Epoxy Group

The added amount of the unsaturated monomer having an epoxy group is not particularly limited. For example, the added amount is preferably set up to a value in the range of 0.1 to 100 parts by weight per 100 parts by weight of the oxetane compound represented by the general formula (1). If the added amount of the unsaturated monomer having an epoxy group is below 0.1 part by weight, advantages based on the addition tends to be poorly exhibited. On the other hand, if the added amount is over 100 parts by weight, the water absorption becomes large or the water repellence decreases. Alternatively, in the case that a photocuring composition is prepared, the film hardness thereof tends to decrease.

Accordingly, the added amount of the unsaturated monomer having an epoxy group is more preferably set up to a value in the range of 0.5 to 100 parts by weight, and still more preferably set up to a value in the range of 1 to 50 parts by weight.

[Sixth Embodiment]

The sixth embodiment relates to an oxetane copolymer obtained by radical-polymerizing an oxetane compound represented by the general formula (1), a fluorine compound represented by the general formula (3) and an unsaturated monomer having a hydroxy group as copolymerization components.

By adding the unsaturated monomer having a hydroxy group the further as the copolymerization component as described above, the adhesion to a glass, a metal, a plastic or the like as a substrate can be improved, using the polarity of the hydroxy group.

In the sixth embodiment, the oxetane compound, the fluorine compound, the process for producing the oxetane copolymer or the like described about the $1^{st}$ to 5th embodiments are also used in the same way. Thus, the description thereon is omitted herein. That is, the unsaturated monomer having a hydroxy group, which is a characteristic in the sixth embodiment, will be mainly described.

(1) Kind of the Unsaturated Monomer Having a Hydroxy Group

Examples of this unsaturated monomer having a hydroxy group include hydroxy group containing vinyl ethers such as 2-hydroxyethyl vinyl ether, 3-hydroxypropyl vinyl ether, 2-hydroxypropyl vinyl ether, 4-hydroxybutyl vinyl ether, 3-hydroxybutyl vinyl ether, 5-hydroxypentyl vinyl ether and 6-hydroxyhexyl vinyl ether; hydroxy group containing allyl ethers such as 2-hydroxyethyl allyl ether, 4-hydroxybutyl allyl ether and glycelol monoallyl ether; allyl alcohols; and hydroxyethyl (meth)acrylate. These unsaturated monomers having a hydroxy group may be used alone or in combination of two or more.

(2) The Added Amount of the Unsaturated Monomer Having a Hydroxy Group

The added amount of the unsaturated monomer having a hydroxy group is not particularly limited. For example, the added amount is preferably set up to a value in the range of 0.1 to 1000 parts by weight per 100 parts by weight of the total of the oxetane compound represented by the general formula (1) and the fluorine compound. If the added amount of the unsaturated monomer having a hydroxy group is below 0.1 part by weight, advantages based on the addition tends to be poorly exhibited. On the other hand, if the added amount is over 1000 parts by weight, the water absorption becomes large so that film strength tends to decrease under wet and hot conditions.

Accordingly, the added amount of the unsaturated monomer having a hydroxy group is more preferably set up to a value in the range of 0.5 to 500 parts by weight, and still more preferably set up to a value in the range of 1 to 500 parts by weight.

[Seventh embodiment]

The seventh embodiment relates to a photocuring composition wherein a light acid generator is added to the oxetane compound obtained in the first embodiment, or any one of the oxetane copolymers which are the $2^{nd}$ to 6th embodiments.

The oxetane compound obtained in the first embodiment, or any one of the oxetane copolymers which are the $2^{nd}$ to 6th embodiments may be used in combination of two or more.

(1) Definition of the Light Acid Generator

The light acid generator used in the photocuring composition which is the seventh embodiment is defined as a compound which is decomposed by radiation of energy rays such as light, so that an oxetane ring is opened to emit an acidic active substance which can be photocured (crosslinked). The seventh embodiment has a characteristic that the light acid generator which can generate an acidic active substance (cation) is used. As the light energy rays radiated to generate the acidic active substance, visible rays, ultraviolet rays, infrared rays, X-rays, α-rays, β-rays or γ-rays are preferably used. The use of ultraviolet rays is preferable since the rays have a given energy level to make rapid hardening possible and further devices for radiation thereof are relatively inexpensive and small-sized.

(2) Kind of the Light Acid Generator

The following will describe the kind of the light acid generator. It is preferred to use, as the light acid generator, an onium salt having a structure represented by the following general formula (10) or a sulfonic acid derivative represented by the following general formula (11):

(10)

wherein the acidic active substance (cation) is an onium ion; W is S, Se, Te, P, As, Sb, Bi, O, I, Br, Cl or —N≡N; $R^7$, $R^8$, $R^9$ and $R^{10}$ are the same or different organic groups; a, b, c and d each is an integer of 0 to 3; (a+b+c+d) is equal to the valence of W; M is a metal or metalloid constituting the central atom of the halogenated complex [$MX_{m+n}$], for example, B, P, As, Sb, Fe, Sn, Bi, Al, Ca, In, Ti, Zn, Sc, V, Cr, Mn or Co; Z is a halogen atom such as F, Cl or Br; m is the net number of the ion of the halogenated complex; and n is the valence of M.

(11)

wherein Q is a monovalent or bivalent organic group; $R^{11}$ is a monovalent organic group having 1 to 12 carbon atoms; subscript s is 0 or 1; and subscript t is 1 or 2.

(3) Added Amount of the Light Acid Generator

The following will describe the added amount (content ratio) of the light generator used in the seventh embodiment. The added amount of the light acid generator is not particularly limited. Usually, the amount is preferably set up to a value in the range of 0.1 to 15 parts by weight per 100 parts by weight of the oxetane compound. If the amount of the light acid generator is below 0.1 part by weight, photocuring ability is lowered so that a sufficient hardening rate tends not to be obtained. On the other hand, if the added amount of the light acid generator is over 15 parts by weight, the weather resistance and the heat resistance of a resultant hardened product tends to decrease.

Therefore, the amount is more preferably set up to a value in the range of 1 to 10 parts by weight per 100 parts by weight of the oxetane compound because of better balance between the photocuring ability and the weather resistance etc. of the hardened product.

(4) Additives or the Like

It is also preferred to added, to the photocuring composition which is the seventh embodiment, additives or the like, for example, a vinyl monomer, a radical photopolymerization initiator, a photosensitizer and an organic solvent unless they damage the object and the advantages of the present invention.

i) Vinyl Monomer & Radical Photopolymerization Initiator

Each of a vinyl monomer, such as an acrylic monomer, and a radical photopolymerization initiator (radical generator) may be added to the photocuring composition which is the seventh embodiment. The radical generator is a compound which is decomposed by receipt of energy rays such as light so as to generate radicals and polymerization-react radical-reactive groups by the radicals. Therefore, the vinyl monomer separately added to the photocuring composition can be subjected to ring-opening, and polymerized or crosslinked.

ii) Photosensitizer

A photosensitizer together with the light acid generator may be blended with the photocuring composition which is the seventh embodiment. The photosensitizer is a compound which absorbs energy rays such as light effectively so that the light acid generator can be effectively decomposed. Examples of such a photosensitizer include thioxantone, diethylthioxantone, and thioxantone derivatives; anthraquinone, bromoanthraquinone and anthraquinone derivatives; anthracene, bromoanthracene, and anthracene derivatives; perylene and perylene derivatives; xanthene, thioxanthene and thioxanethene derivatives; and coumarin and ketocoumarin.

Among these photosensitizers, more preferable compounds are diethylthioxanethone and bromoanthracene.

The added amount of the photosensitizer is not particularly limited. The added amount is preferably set up to a value in the range of 0.01 to 300 parts by weight per 100 parts by weight of the light acid generator. If the added amount of the photosensitizer is below 0.01 part by weight, advantages based on the addition tends not to be exhibited. On the other hand, if the added amount is over 300 parts by weight, the weather resistance or the like tends to decrease.

Therefore, the amount of the photosensitizer is more preferably set up to a value in the range of 0.5 to 100 parts by weight per 100 parts by weight of the light acid generator because of better balance between the exhibition of the advantages based on the addition and the weather resistance or the like. The amount is still more preferably set up to a value in the range of 1.0 to 50 parts by weight.

iii) Organic Solvent

It is preferred to blend an organic solvent with the photocuring composition which is the seventh embodiment. By adding the organic solvent, it is possible to mix the oxetane compound or oxetane copolymer with the light acid generator more homogeneously. It is also possible to adjust the viscosity of the photocuring composition and improve convenience and film properties.

Therefore, the viscosity of the photocuring composition is preferably set up to a value in the range of 1 to 10,000 cps (25° C.) by blending the organic solvent. If the viscosity exceeds this range, the formation of a homogeneous film may become difficult.

The organic solvent for use can be selected from the scope that does not damage the objects and the advantages of the present invention. The organic solvent is preferably an organic compound which usually has a boiling point in the range of 50 to 200° C. under the atmospheric pressure and which causes the respective components to be homogeneously dissolved.

(4) Method of Use

When the photocuring composition which is the seventh embodiment is used, the method of coating this composition on a substrate (a portion to be applied) is generally adopted.

It is preferred to use, as the method of applying the photocuring composition, dipping, spraying, bar coating, roll coating, spin coating, curtain coating, gravure printing, silk screen printing, ink-jet printing or the like.

Next, a hardened film can be formed on the substrate by radiating ultraviolet rays or the like onto the applied photocuring composition in the manner that the light exposure amount is from 100 to 1,000 mJ/cm$^2$.

The means for photocuring the photocuring composition is not particularly limited. Various ordinary means may be adopted.

It is preferred to use a light source such as a high-pressure mercury lamp, a low-pressure mercury lamp, a metal halide lamp or an excimer lamp to radiate light onto the whole surface of the film. It is also preferred to radiate laser, or convergence light or the like light which is obtained with a lens, a mirror or the like to the photocuring composition while such light is scanned. Furthermore, it is also preferred to use a photomask having a light transmission portion patterned into a given form to radiate non-convergence light to the composition through the photomask, or use a light conductor composed of a bundle of many optical fibers to radiate light to the composition through optical fibers corresponding to the given pattern of the light conductor.

Eighth Embodiment

The eighth embodiment relates to an embodiment of a photocuring composition wherein a reactive diluent is further contained in the seventh embodiment.

By adding (blending) the reactive diluent as described above, it is possible to adjust physical properties of a resultant photocured product or adjust light reactivity of the photocuring composition.

In the eighth embodiment, the oxetane compound, the oxetane copolymer, the light acid generator, the method of use or the like described about the 1$^{st}$ to 7th embodiments are used as they are. Thus, the description thereon is omitted herein. That is, the reactive diluent, which is a characteristic in the eighth embodiment, will be mainly described.

(1) Blended Amount of the Reactive Diluent

The blended amount (the added amount) of the reactive diluent is not particularly limited in the eighth embodiment. For example, the amount is preferably set up to a value in the range of 0.1 to 2,000 parts by weight per 100 parts by weight of the oxetane compound. If the amount of the reactive diluent is below 1 part by weight, advantages based on the addition tend not to be exhibited. On the other hand, if the added amount is over 2,000 parts by weight, the weather resistance and the heat resistance of a resultant hardened product tends to decrease. Therefore, the blended amount of the reactive diluent is more preferably set up to a value in the range of 1.0 to 1,500 parts by weight and still more preferably set up to a value in the range of 2.0 to 1,000 parts by weight.

(2) Kind of the Reactive Diluent

The following will describe the reactive diluent used in the eighth embodiment. It is preferred to blend, as the reactive diluent, i) a cationic polymerizable monomer and ii) an ethylenic unsaturated monomer, or either one monomer thereof. The kind of the ethylenic unsaturated monomer was described about the second embodiment. Thus, the description thereon is omitted herein.

i) Cationic Polymerizable Monomer

The cationic polymerizable monomer, which is the reactive diluent, is defined as an organic compound that causes polymerization reaction or crosslinking reaction by radiation of light in the presence of the light acid generator. Therefore, examples thereof include epoxy compounds, oxetane compounds, oxolane compounds, cyclic acetal compounds, cyclic lactone compounds, thiirane compounds, thiethane compounds, vinyl ether compounds, spiroorthoester compounds, which are reaction products of an epoxy compound and lactone, ethylenic unsaturated compounds, cyclic ether compounds, cyclic thioether compounds, and vinyl compounds. These cationic polymerizable monomers are used alone or used preferably in combination of two or more.

ii) Ethylenic Unsaturated Monomer

As the reactive diluent, the ethylenic unsaturated monomer as the copolymerization monomer described about the second embodiment can be used as it is. By using the ethylenic unsaturated monomer as described above, radical polymerization reaction can be used together in photocuring. Accordingly, a higher photopolymerization rate can be obtained.

In the case that the ethylenic unsaturated monomer is used in the eighth embodiment, it is preferred to add a radical photopolymerization initiator (radical generator) further.

Examples

Examples of the present invention will be described hereinafter. The present invention is not limited to these examples. In the examples, the blended amounts of respective components are represented by parts by weight unless specified otherwise.

Example 1

(Synthesis of an Oxetane Compound)

An oxetane compound was synthesized by the oxetane compound producing process of the present invention. Namely, 1.2 L of hexane and 1560 g of a 50 weight % aqueous sodium hydroxide solution were charged into a 5 L separable flask with a stirrer, a thermometer, a cooler and a dropping funnel. Thereafter, 53 g of tetra-n-butylammonium bromide (0.16 mole) was added as a phase transfer catalyst thereto.

Next, a mixed solution of 139 g of 3-methyl-3-oxetane methanol (1.36 mole) and 369 g of 2-chloroethyl vinyl ether (3.46 g) was dropwise added into the separable flask at room temperature (25° C.).

After the end of the addition, the separable flask was heated with an oil bath, so that the temperature inside the separable flask was raised to 67° C. While reflux was conducted at this temperature for 5 hours, 3-methyl-3-oxetane methanol and 2-chloroethyl vinyl ether was reacted to obtain a reaction solution.

The resultant reaction solution was cooled with ice, and then 2.4 L of water cooled with ice in the same way was added to the reaction solution. The mixed gas was vigorously shaken. Thereafter, the water phase and the organic phase were separated and then only the organic phase was collected. To the resultant organic phase was added 50 g of calcium carbonate, so that this phase was dehydrated. Hexane, which is an organic solvent, was removed from the dried organic phase by vacuum concentration. Furthermore, the organic phase was subjected to vacuum distillation under conditions that temperature was 67° C. and pressure was 5 mmHg, to obtain a purified product.

(Estimation of the Oxetane Compound)

The resultant purified product was subjected to measurement of an infrared absorption spectrum, measurement of proton-NMR, and elementary analysis. About the resultant purified product, the radical reactivity and the copolymerization-ability with other vinyl monomers were evaluated.

(1) Measurement of an Infrared Absorption Spectrum

The above-mentioned Fourier transformation type infrared spectrometer JIR-5500 was used to make a measurement under conditions that room temperature was 25° C., resolution power was 4 cm$^{-1}$, gain was 1 time, and the number of scanning was 2 by the KBr method. FIG. 1 shows a measured infrared absorption spectrum.

Figure 3:
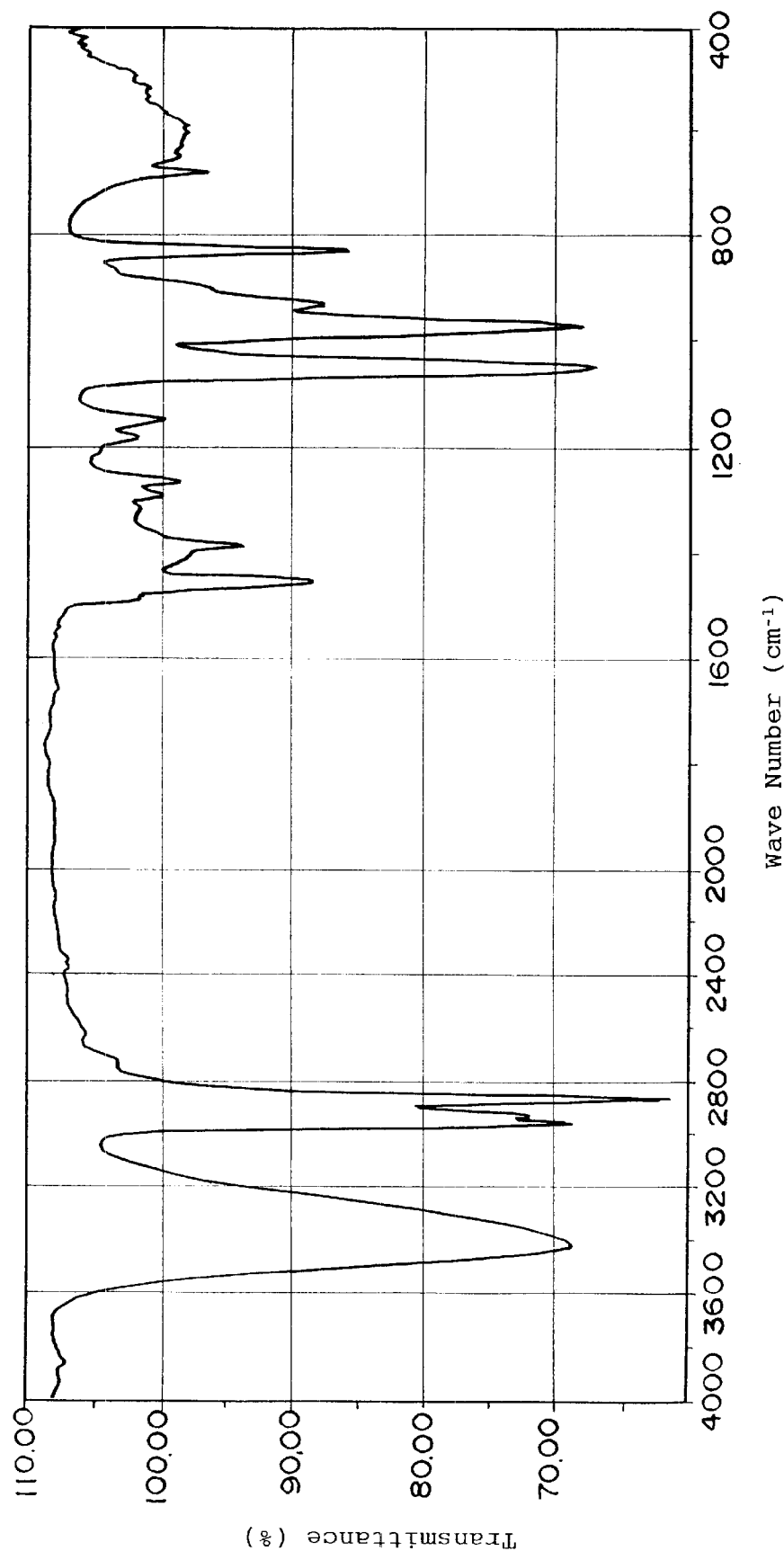
FIG. 3 is an infrared absorption spectrum of 3-methyl-3-oxetane methanol.
Figure 4:
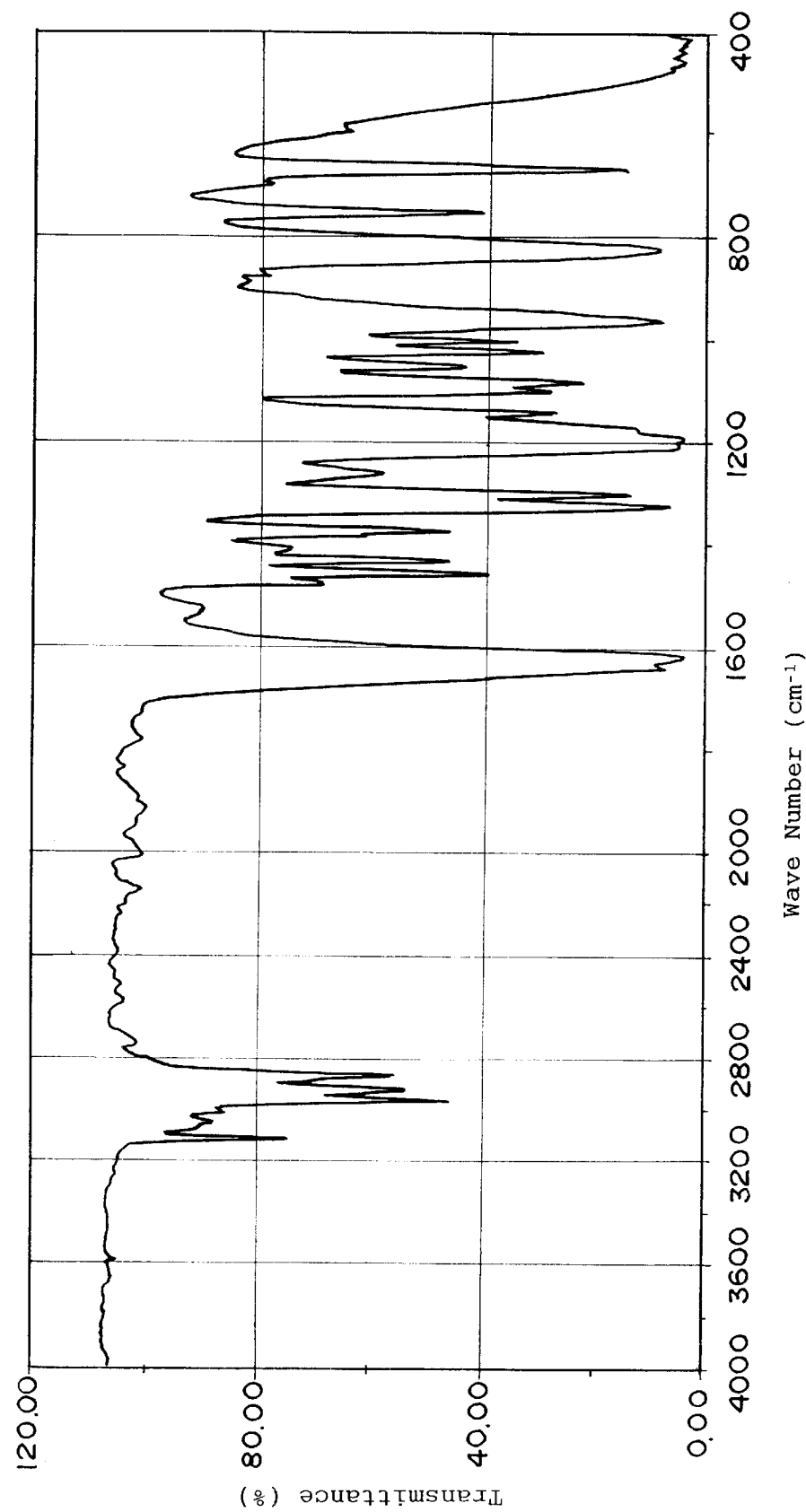
FIG. 4 is an infrared absorption spectrum of 2-chloroethyl vinyl ether.

For reference, FIG. 3 shows the infrared absorption spectrum of 3-methyl-3-oxetane methanol represented by the following formula (13), which was used as a raw material upon synthesis of 2-(3-methyl-3-oxetanemethoxy) ethyl vinyl ether. In the same way, FIG. 4 shows the spectrum of 2-chloroethyl vinyl ether represented by the following general formula (14).

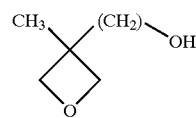
(13)

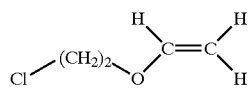
(14)

As can be understood from the infrared absorption spectrum shown in FIG. 1, a remarkable peak assigned to vibration of the oxetane ring appears at a wavenumber of 977 cm$^{-1}$. A remarkable peak assigned to stretching vibration of the vinyl group also appears at a wavenumber of 1,618 cm$^{-1}$. Furthermore, a peak assigned to the ether bond of the oxetane group appears at a wavenumber of 1,128 cm$^{-1}$. Peaks assigned to the ether bond adjacent to the vinyl group appear at wavenumbers of 1,047 cm$^{-1}$ and 1,203 cm$^{-1}$.

Thus, considering a proton-NMR spectrum and results of elementary analysis described later, it was acknowledged that the resultant purified product was 2-(3-methyl-3-oxetanemethoxy)ethyl vinyl ether.

(2) Measurement of the Proton-NMR Spectrum

The proton-NMR spectrum was measured with a proton-NMR measuring machine JNM-EX90 (made by JEOL Ltd.) under conditions that a solvent was CDCl$_3$ and resolution power was 90 MHz. FIG. 2 shows a chart of the measured proton-NMR.

Figure 5:
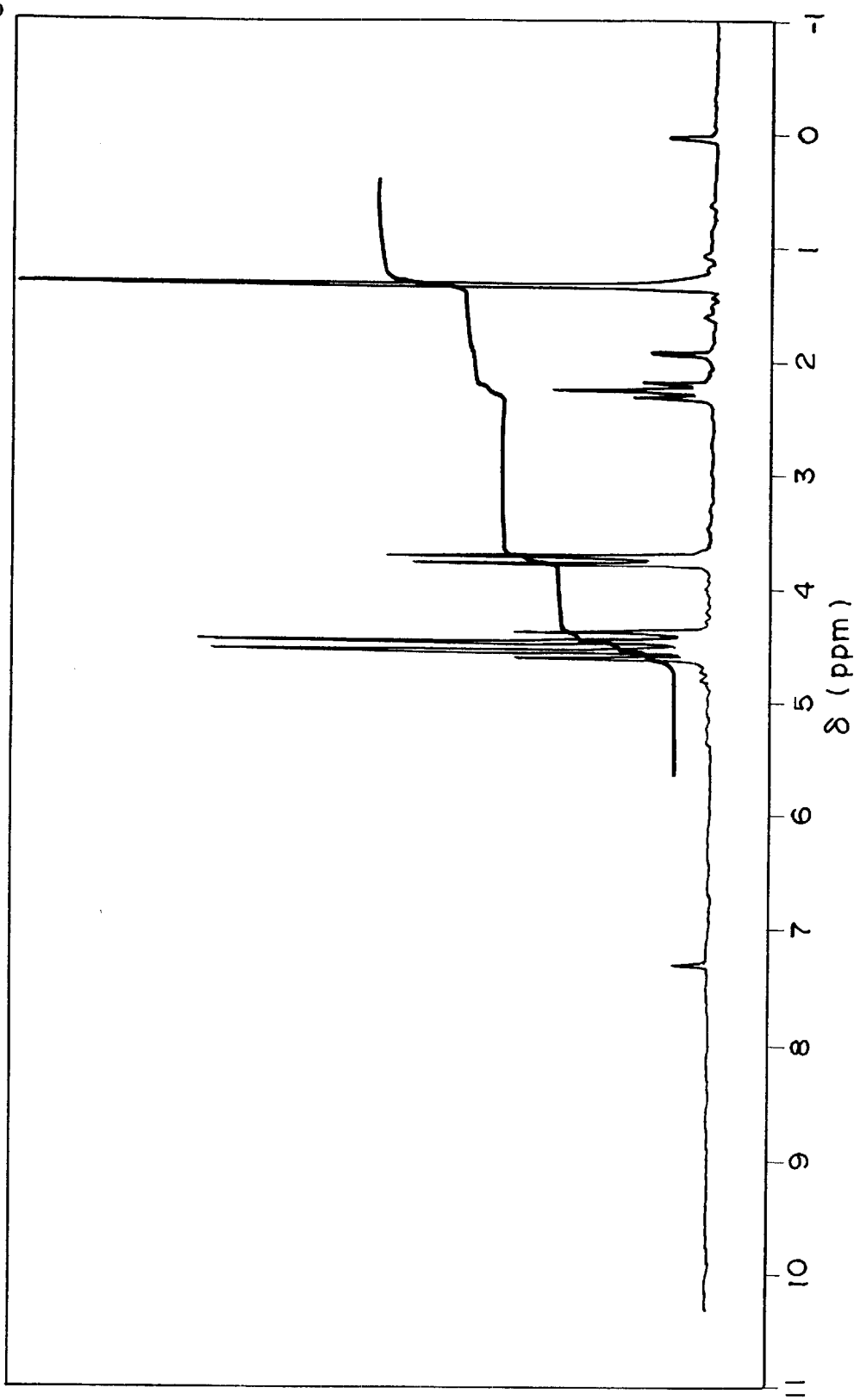
FIG. 5 is a proton-NMR spectrum of 3-methyl-3-oxetane methanol.
Figure 6:
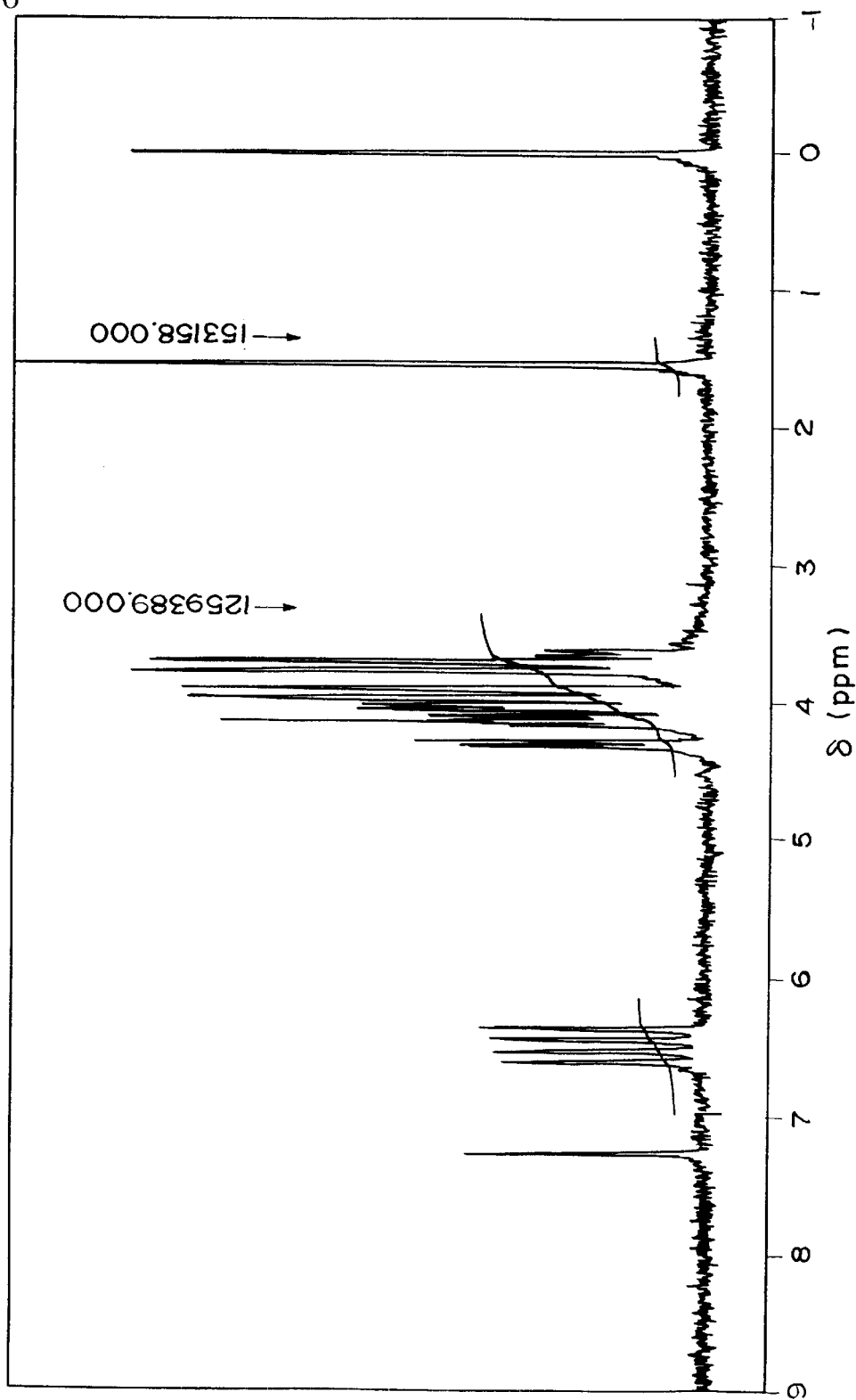
FIG. 6 is a proton-NMR spectrum of 2-chloroethyl vinyl ether.

For reference, FIG. 5 shows the proton-NMR spectrum of 3-methyl-3-oxetane methanol, which was used as a raw material upon synthesis of 2-(3-methyl-3-oxetanemethoxy) ethyl vinyl ether. In the same way, FIG. 6 shows the proton-NMR spectrum of 2-chloroethyl vinyl ether.

As can be understood from the proton-NMR spectrum shown in FIG. 2, the following data were obtained:

δ=1.3 (the shape of the peak: s, 3H, assigned to hydrogen atoms in CH$_3$ in the CH$_3$-oxetane ring), δ=3.5 (the shape of the peak: s, 2H, assigned to hydrogen atoms in CH$_2$ adjacent to the oxetane ring), δ=3.7 (the shape of the peak: m, 2H, assigned to hydrogen atoms in CH$_2$ next to the left end in —CH$_2$—CH$_2$—O—CH=CH$_2$), δ=3.9 (the shape of the peak: m, 2H, assigned to hydrogen atoms in the left end CH$_2$ in —CH$_2$—CH$_2$—O—CH=CH$_2$), δ=4.0–4.2 (the shape of the peak: quadruple lines, 2H, assigned to hydrogen atoms in the right side CH$_2$ in —CH=CH$_2$), δ=4.3–4.5 (the shape of the peak: dd, 4H, assigned to hydrogen atoms in CH$_2$ in the oxetane ring), and δ=6.5 (the shape of the peak: dd, 1H, assigned to a hydrogen atom in CH in —CH=CH$_2$).

(3) Elementary Analysis

An elementary analysis machine CHN coder MT-3 type (Yanaco Analytical Instruments Corp.) was used to calculate the weight ratios of carbon and hydrogen.

As a result, the weight ratios that carbon was 60.12% by weight and hydrogen was 9.34% by weight were obtained. It was also acknowledged that they were highly consistent with the values that carbon was 62.74% by weight and hydrogen was 9.37% by weight, which were theoretical weights (calculated values) in the case that the resultant product was regarded as 2-(3-methyl-3-oxetanemethoxy) ethyl vinyl ether.

(4) Evaluation of Radical Reactivity

An autoclave made of stainless steel, with an electromagnetic stirrer, having an internal volume of 0.5 L was subjected to sufficient nitrogen-substitution, using nitrogen gas. Next, into this autoclave were charged 20 g of the resultant purified product 2-(3-methyl-3-oxetanemethoxy)ethyl vinyl ether, 0.2 g of benzoyl peroxide as a radical generator, and 200 g of ethyl acetate as an organic solvent. The inside of the autoclave was sufficiently stirred and then dry ice and methanol were used to cool the temperature inside the autoclave to −50° C. Nitrogen gas was again used to remove oxygen in the system.

Next, the temperature inside the autoclave was raised to 70° C. While the inside thereof was stirred, 2-(3-methyl-3-oxetanemethoxy)ethyl vinyl ether was radical-polymerized over 20 hours. Thereafter, the autoclave was cooled with water to quench the reaction, and then an oxetane polymer solution (polymer solution) was obtained.

The resultant oxetane polymer solution was poured into a great volume of methanol to precipitate an oxetane polymer. Thereafter, the oxetane polymer was washed with a great volume of methanol, and then vacuum-dried at a temperature of 50° C. to obtain a purified oxetane polymer.

Therefore, it was acknowledged that the resultant purified product 2-(3-methyl-3-oxetanemethoxy)ethyl vinyl ether had excellent radical polymerization-ability.

Example 2

(Production of an Oxetane Copolymer)

An autoclave made of stainless steel, with an electromagnetic stirrer, having an internal volume of 0.5 L was subjected to sufficient nitrogen-substitution, using nitrogen gas. Next, into this autoclave were charged 19.0 g of the resultant purified product 2-(3-methyl-3-oxetanemethoxy)ethyl vinyl ether, and 31.8 g of ethyl vinyl ether. Thereinto was further charged 10 g of a nonionic reactive emulsifier (NE-30, made by Asahi Denka Kogyo KK), 1.0 g of azo group containing polydimethylsiloxane (VPS-1001, made by Wako Pure Chemicals Industries Ltd.) as a radical generator, and 0.5 g of lauroyl peroxide. At last, thereinto was charged 300 g of ethyl acetate as an organic solvent. The copolymerization components were sufficiently stirred and then dry ice and methanol were used to cool the temperature inside the autoclave to −50° C. Nitrogen gas was again used to remove oxygen in the system.

Next, 99.3 g of hexafluoropropylene (gas) was introduced into the autoclave and then the temperature inside the autoclave was raised to 70° C. The pressure inside the autoclave when the temperature was 70° C. was 5.8 kgf/cm$^2$.

While the copolymerizable components inside the autoclave were stirred and the temperature was kept at 70° C., the copolymerizable components were radical-polymerized over 20 hours. When the pressure inside the autoclave was lowered to be 2.5 kgf/cm$^2$, the autoclave was cooled with water to quench the reaction. After it was acknowledged that the temperature inside the autoclave was lowered to room temperature, the autoclave was opened to emit unreacted monomers outside the system and obtain an oxetane copolymer solution (polymer solution).

The resultant oxetane copolymer solution was poured into a great volume of methanol to precipitate an oxetane copolymer. Thereafter, the oxetane copolymer was washed with a great volume of methanol, and then vacuum-dried at a temperature of 50° C. to obtain a purified oxetane copolymer.

Therefore, it was acknowledged that in the resultant oxetane copolymer, 2-(3-methyl-3-oxetanemethoxy)ethyl vinyl ether as a copolymerization component and hexafluoropropylene as a fluorinated compound had excellent compatibility with each other and could be homogeneously polymerized. The resultant oxetane copolymer was measured 5 times about each of the following evaluation items. As a result, it was also acknowledged that the copolymer had uniform properties (values).

(Evaluation of the Oxetane Copolymer)

(1) Measurement of the Number Average Molecular Weight

The resultant oxetane copolymer was dissolved in THF (tetrahydrofuran) so that the concentration thereof was 0.5% by weight. Next, a GPC device HLC-8020 (made by Tosoh Corp.) was used to detect elution time from its GPC column with a refractometer (RI). From the resultant elution time, the number average molecular weight was calculated as a molecular weight converted to polystyrene. As a result, the number average molecular weight of the resultant oxetane copolymer was 40,000.

(2) $^{13}$C-NMR Measurement

Figure 7:
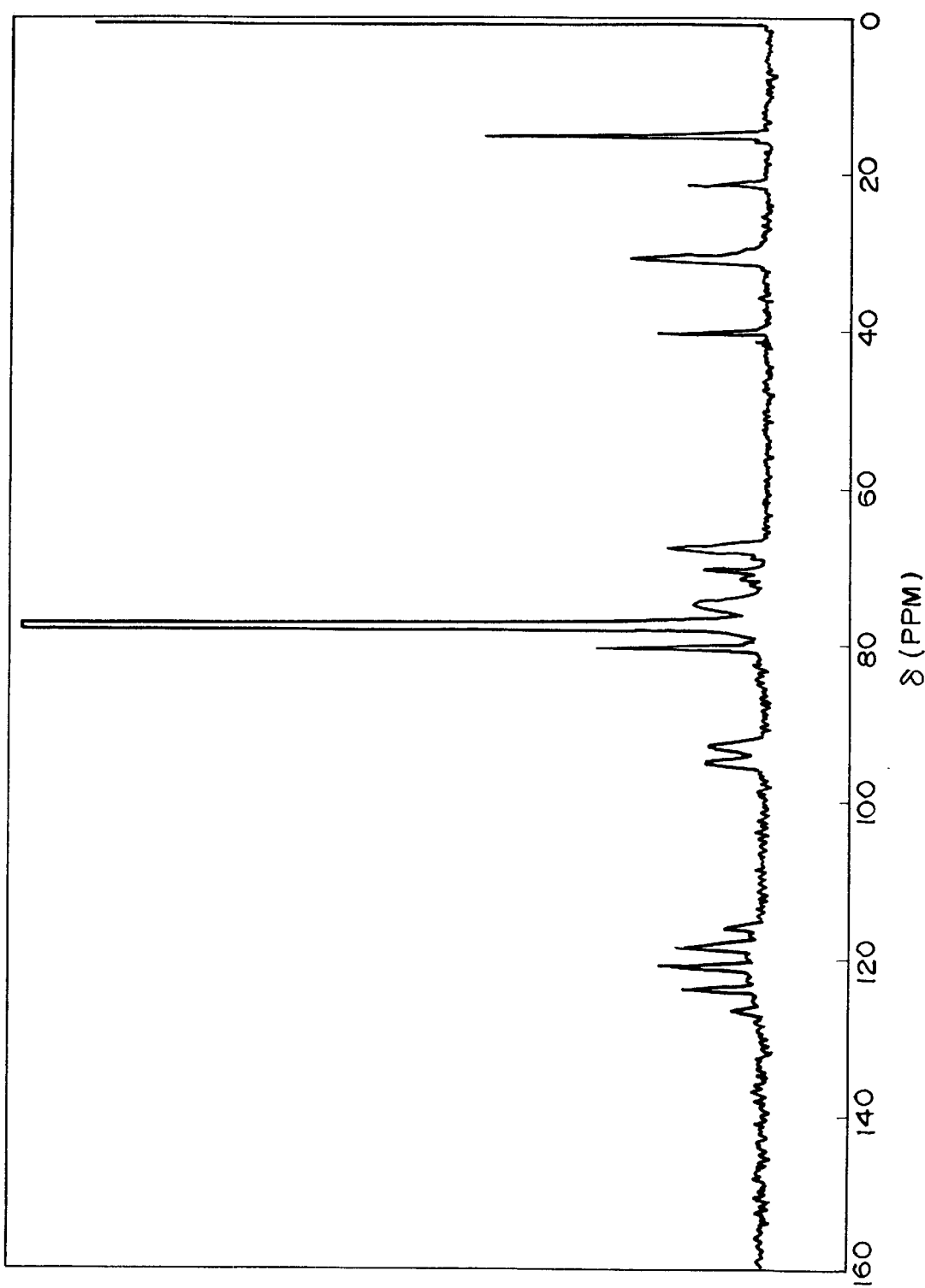
FIG. 7 is a $^{13}$C-NMR spectrum of an oxetane copolymer (Example 2).

About the resultant oxetane copolymer, a $^{13}$C-NMR measuring machine MSL400 type FT-NMR (made by Brucker Instruments Inc.) was used to make a measurement. As a result, the following were acknowledged: a peak originating from the carbon of oxetane ether at 80 ppm, and peaks originating from the carbons in the main chain of the fluorinated compound and originating from the carbon in $CF_3$ at 92 to 95 and 115 to 126 ppm, respectively. Furthermore, it was acknowledged that peaks originating from the vinyl carbons in the oxetane compound (85 and 150 ppm) were lost while a single bond main chain carbon peak originating from the polymerized vinyl ether (30 and 75 ppm) was recognized. Therefore, it was acknowledged that the oxetane copolymer was polymerized. For reference, FIG. 7 shows the resultant $^{13}$C-NMR spectrum.

(3) Measurement of an Infrared Absorption Spectrum

Figure 8:
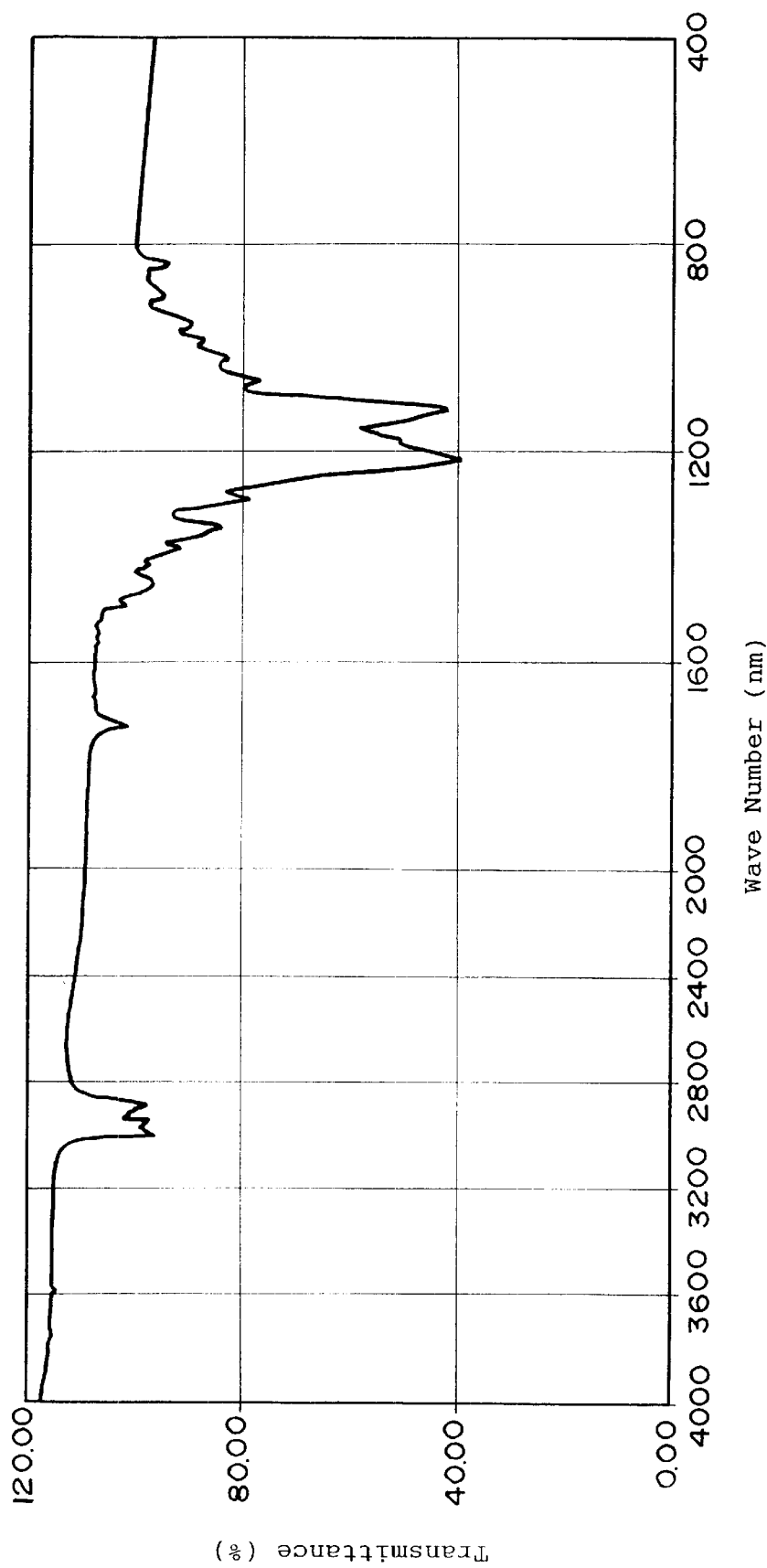
FIG. 8 is a proton-NMR spectrum of the oxetane compound (Example 2).

About the resultant oxetane copolymer, a Fourier transformation type infrared spectrometer JIR-5500 was used to make a measurement under conditions that room temperature was 25° C., resolution power was 4 cm$^{-1}$, gain was 1 time, and the number of scanning was 2 by the KBr method. FIG. 8 shows a measured infrared absorption spectrum.

(4) Fluorine Content

The fluorine content in the resultant oxetane copolymer was measured according to the alizarin complexion method. As a result, the fluorine content by percentage in the resultant oxetane copolymer was 48.0% by weight.

(5) Measurement of the Glass Transition Temperature

A DSC device 910 (made by Du Pont Co., Ltd.) was used to measure the glass transition temperature of the resultant oxetane copolymer under conditions that temperature rising rate was 10° C./minute and nitrogen gas flow was used. As a result, the glass transition temperature of the resultant oxetane copolymer was 28.0° C.

(6) Measurement of the Contact Angle

A CA-X type contact angle meter made by FASE Co., Ltd. was used to measure the contact angle of the resultant oxetane copolymer with pure water under conditions that temperature was 23° C. and humidity was 50% RH. As a result, the contact angel of the oxetane copolymer was 97°. If the contact angle is 90° or more, it can be said that excellent water repellence is generally exhibited.

(7) Measurement of the Light Transmittance

A spectrophotometer was used to measure the light transmittance of the resultant oxetane copolymer. As a result, it was acknowledged that the light transmittance was 95% or more.

(8) Measurement of the Water Absorbance

The water absorbance of the resultant oxetane copolymer was measured according to JIS K7209 (Measurement of water absorbance of plastic). As a result, it was acknowledged that the water absorbance was 0.6% by weight.

(9) Evaluation 1 of Cationic Polymerization-Ability

Three parts by weight of Sunaid SI-80L (Sanshin Chemical Industry Co., Ltd.), which was a heat acid generator, were added to 100 parts of the resultant oxetane copolymer, and the resultant mixture was homogeneously mixed. The resultant mixed solution was applied onto a quartz plate with a bar coater (No. 10), to form a film having a uniform thickness. This film was heated under conditions of 100° C. and 1 hour with an oven. As a result, a colorless and transparent hardened film was obtained.

Therefore, it was acknowledged that the resultant oxetane copolymer had excellent cationic polymerization-ability.

(10) Evaluation 2 of Cationic Polymerization-Ability

Three parts by weight of Sunaid SI-100L (Sanshin Chemical Industry Co., Ltd.), which was a light acid generator, were added to 100 parts of the resultant oxetane copolymer, and the resultant mixture was homogeneously mixed. The resultant mixed solution was applied onto a quartz plate with a bar coater (No. 10), to form a film having a uniform thickness. A high-pressure mercury lamp (made by ORC Manufacturing Co., Ltd.) was used to irradiate this film with ultraviolet rays under conditions that exposure amount would be 200 mJ/cm$^2$. As a result, a colorless and transparent hardened film was obtained.

Therefore, it was acknowledged that the resultant oxetane copolymer had excellent cationic polymerization-ability.

(11) Preservation Stability

One hundred parts by weight of the resultant oxetane copolymer were dissolved to 150 parts by weight of MIBK, to prepare a copolymer solution containing 40% by weight of solid contents. To this copolymer solution were 3 parts by weight of Sunaid SI-80L (Sanshin Chemical Industry Co., Ltd.) as a heat acid generator, and then they were homogeneously mixed. The resultant mixed solution was allowed to stand still in a thermostat having a temperature of 50° C. for one week, and then a change in its appearance and an increase in its viscosity were visually observed.

As a result, such a change in the appearance and an increase in the viscosity were not particularly observed. Therefore, it was acknowledged that the resultant oxetane copolymer had excellent preservation stability.

Examples 3 to 7

The kinds or the blended amounts of the copolymerization components were changed as shown in Table 1, and oxetane copolymers were polymerized in the same way as Example 1. The resultants were evaluated. Namely, the following were evaluated: the copolymerization-ability of an unsaturated monomer having a hydroxy group and the addition advantages thereof in Example 3, the copolymerization-ability of an unsaturated monomer having a hydrolyzable silyl group and the addition advantages thereof in Example 4, the copolymerization-ability of an unsaturated monomer having an epoxy group and the addition advantages thereof in Example 5, the effect of the kind of the fluorine compound in Example 6, and the copolymerization-ability of an unsaturated monomer having a hydrolyzable silyl group and an unsaturated monomer having an epoxy group and the addition advantages thereof in Example 7. Respective results are shown in Table 1.

TABLE 1

| | Monomer | Example 2 | 3 | 4 | 5 | 6 | 7 | Comparative Example 2 | 3 |
|---|---|---|---|---|---|---|---|---|---|
| Charging amount (g) | HFP | 99.3 | 88.7 | 86.7 | 89.8 | 69.8 | 95.2 | 90.3 | 98.9 |
| | FPVE | — | — | — | — | 25.8 | — | — | — |
| | OXVE | 19.0 | 33.9 | 33.1 | 34.3 | 25.0 | 18.2 | — | — |
| | EVE | 31.8 | 14.2 | 13.9 | 14.4 | 24.4 | 22.8 | 14.4 | 15.8 |
| | VTMS | — | — | 14.3 | — | — | 7.8 | — | — |
| | GVE | — | — | — | 10.0 | — | 5.3 | — | 22.0 |
| | HBVE | — | 11.4 | — | — | — | — | 11.6 | 12.8 |
| | PEPC | — | — | — | — | — | — | 31.7 | — |
| | NE-30 | 10.0 | 10.0 | 10.0 | 10.0 | 10.0 | 10.0 | 10.0 | 10.0 |
| | LPO | 0.5 | 0.5 | 0.5 | 0.5 | 0.5 | 0.5 | 0.5 | 0.5 |
| | VPS-1001 | 1.0 | 1.0 | 1.0 | 1.0 | 1.0 | 1.0 | 1.0 | 1.0 |
| Yield (g) | | 128 | 116 | 111 | 122 | 115 | 119 | No copolymer was obtained | 122 |
| Recovery percentage | | 85 | 78 | 75 | 82 | 79 | 80 | | 81 |
| Number average molecular weight ($\times 10^4$) | | 4.0 | 5.1 | 3.2 | 4.5 | 3.8 | 4.4 | | 5.6 |
| Fluorine content (%) | | 48.0 | 42.0 | 43.2 | 44.1 | 50.1 | 46.7 | | 48.5 |
| Glass transition temperature (° C.) | | 28 | 33 | 30 | 35 | 22 | 31 | | 33 |
| Contact angle with pure water | | 97 | 91 | 94 | 95 | 110 | 108 | | 96 |
| Transmittance (%) | | 95 or more | 95 or more | 95 or more | 95 or more | 95 or more | 95 or more | | 92 |
| Water absorbance (%) | | 0.6 | 0.8 | 0.8 | 0.7 | 0.5 | 0.6 | | 0.8 |
| Preservation stability | | Not changed | Not changed | Not changed | Not changed | Not changed | Not changed | | Gelatinization |

Abbreviations in Table 1 indicate the following compounds.
OXVE: 2-(3-methyl-3-oxetanemethoxy)ethyl vinyl ether
HFP: hexafluoropropane
FPVE: perfluoro(propyl vinyl ether)
EVE: ethyl vinyl ether
VTMS: vinyltrimethoxysilane
GVE: glycidyl vinyl ether
HBVE: hydroxybutyl vinyl ether TABLE 1-continued

| | Example | | | | | | Comparative Example | |
|---|---|---|---|---|---|---|---|---|
| Monomer | 2 | 3 | 4 | 5 | 6 | 7 | 2 | 3 |

PEPC: propenyl ether propylenecarbonate
LPO: lauroyl peroxide

Comparative Example 1

The radical polymerizability of propenyl ether propylenecarbonate (made by ISP Co., Ltd.) as a compound having in the molecule thereof one ether bond besides an oxetane group was evaluated.

First, an autoclave made of stainless steel, with an electromagnetic stirrer, having an internal volume of 0.5 L was subjected to sufficient nitrogen-substitution, using nitrogen gas. Next, into this autoclave were charged 20.0 g of propenyl ether propylenecarbonate, 0.2 g of benzoyl peroxide as a radical generator, and 200 g of ethyl acetate as an organic solvent. The inside of the autoclave was sufficiently stirred and then dry ice and methanol were used to cool the temperature inside the autoclave to −50° C. Nitrogen gas was again used to remove oxygen in the system.

Next, the temperature inside the autoclave was raised to 70° C. While the inside of the autoclave was stirred, propenyl ether propylenecarbonate was radical-polymerized over 20 hours. In the same way as in Example 1, the solution after the radical polymerization was poured into a great volume of methanol to perform re-precipitation and purification. However, any polymer as a solid content could not be obtained. Thus, it was acknowledged that propenyl ether propylenecarbonate was poor in radical polymerizability.

In the same way as in Example 1, hexafluoropropylene (gas) was introduced into the autoclave. Thereafter, copolymerization reaction was conducted. However, any copolymer as a solid content could not be obtained. Thus, it was acknowledged that propenyl ether propylenecarbonate was poor in not only radical polymerizability but also compatibility with any fluorine-containing unsaturated monomer.

Comparative Example 2

(Production of an Oxetane Copolymer)

In the same way as in Example 1, an autoclave made of stainless steel, with an electromagnetic stirrer, having an internal volume of 0.5 L was subjected to sufficient nitrogen-substitution, using nitrogen gas. Next, into this autoclave were separately charged 31.7 g of propenyl ether propylenecarbonate (made by ISP Co., Ltd.) represented by the following general formula (15) shown below, 14.4 g of ethyl vinyl ether, 11.6 g of hydroxybutyl vinyl ether. Thereinto was further charged 10 g of a nonionic reactive emulsifier (NE-30, made by Asahi Denka Kogyo KK), 1.0 g of azo group containing polydimethylsiloxane (VPS-1001, made by Wako Pure Chemicals Industries Ltd.) as a radical generator, and 0.5 g of lauroyl peroxide. At last, thereinto was charged 300 g of ethyl acetate as an organic solvent. The copolymerization components were sufficiently stirred and then dry ice and methanol were used to cool the temperature inside the autoclave to −50° C. Nitrogen gas was again used to remove oxygen in the system.

Next, 90.3 g of hexafluoropropylene (gas) was introduced into the autoclave and then the temperature inside the autoclave was raised to 70° C. While the copolymerization components inside the autoclave were stirred, the copolymerization components were radical-polymerized under conditions that temperature was 70° C. and time was 20 hours. Thereafter, the autoclave was cooled with water to quench the reaction. After it was acknowledged that the temperature inside the autoclave was lowered to room temperature, the autoclave was opened to emit unreacted monomers outside the system and obtain a copolymer solution.

The resultant oxetane copolymer solution was poured into a great volume of methanol to perform re-precipitation and purification. As a result, any copolymer as a solid content could not be obtained. Thus, the same evaluation of a copolymer as in Example 1 could not be made. That is, it was acknowledged that propenyl ether propylenecarbonate was poor in radical polymerizability and copolymerizability with other unsaturated monomers.

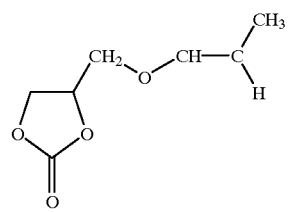

(15)

Comparative Example 3

In the same way as in Example 1, an autoclave made of stainless steel, with an electromagneti(1) stirrer, having an internal volume of 0.5 L was subjected to sufficient nitrogen-substitution, using nitrogen gas. Next, into this autoclave were charged 15.8 g of ethyl vinyl ether, 12.8 g of hydroxybutyl vinyl ether and 22.0 g of glycidyl vinyl ether. Thereinto was further charged 10 g of a nonionic reactive emulsifier (NE-30, made by Asahi Denka Kogyo KK), 1.0 g of azo group containing polydimethylsiloxane (VPS-1001, made by Wako Pure Chemicals Industries Ltd.) as a radical generator, and 0.5 g of lauroyl peroxide. At last, thereinto was charged 300 g of ethyl acetate as an organic solvent. The copolymerization components or the like were sufficiently stirred and then dry ice and methanol were used to cool the temperature inside the autoclave to −50° C. Nitrogen gas was again used to remove oxygen in the system.

Next, 98.9 g of hexafluoropropylene (gas) was introduced into the autoclave and then the temperature inside the autoclave was raised to 70° C. While the copolymerization components or the like inside the autoclave were stirred, the copolymerization components were radical-polymerized under conditions that temperature was 70° C. and time was 20 hours. Thereafter, the autoclave was cooled with water to quench the reaction. After it was acknowledged that the temperature inside the autoclave was lowered to room temperature, the autoclave was opened to emit unreacted monomers outside the system and obtain a copolymer solution.

The resultant oxetane copolymer solution was poured into a great volume of methanol to precipitate a copolymer. Thereafter, the copolymer was washed with a great volume of methanol, and further vacuum-dried at a temperature of 50° C. to obtain a purified oxetane copolymer.

The resultant copolymer was evaluated in the same way as in Example 2 so that it was gelatinized in the preservation stability test. Therefore, it was acknowledged that the copolymer having a glycidyl group had poor preservation stability.

INDUSTRIAL APPLICABILITY

According to the above-mentioned present invention, it becomes possible to obtain an oxetane which is excellent in radical polymerization-ability and cationic polymerization-ability and in copolymerization-ability with other unsaturated monomers (vinyl monomers or the like), in particular with a fluorine-containing vinyl monomer. Moreover, by reacting an oxetane alcohol compound with a halogenated vinyl ether compound in the presence of a phase transfer catalyst according to the process for producing an oxetane compound of the present invention, it becomes possible to obtain an oxetane compound effectively. Furthermore, it becomes possible to obtain an oxetane copolymer which comprises the oxetane compound and fluorine compound as copolymerizable(copolymerization) components and which has a low water absorbance and is excellent in water repellence and transparency.

Since such an oxetane copolymer has in the molecule thereof an oxetane group that can be photocured, the copolymer can be easily photocured. By using a nonionic reactive emulsifier as a copolymerization component of such an oxetane copolymer, it becomes possible to obtain an oxetane copolymer having good application ability and leveling ability.

By using an unsaturated monomer having a hydrolyzable silyl group as a copolymerization component of such an oxetane copolymer, it is possible to introduce a cationic reactive group into the molecule. Therefore, it is possible to make the photocuring rate in the oxetane copolymer high.

By using an unsaturated monomer having an epoxy group as a copolymerization component of such an oxetane copolymer, it is possible to introduce a cationic reactive group into the molecule. Therefore, it is possible to make the photocuring rate in the oxetane copolymer high.

By using an unsaturated monomer having a hydroxy group as a copolymerization component of such an oxetane copolymer, it is possible to introduce a polar group into the molecule. Therefore, it is possible to improve the adhesion of the oxetane copolymer to a substrate.

What is claimed is:

1. An oxetane compound represented by the following formula (1):

(1)

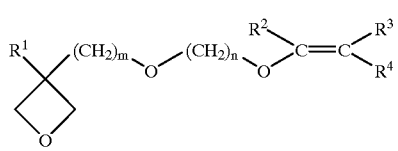

wherein substituent $R^1$ is hydrogen, alkyl, fluorine, fluoroalkyl, ally, aryl, furyl or thienyl; substituents $R^2$, $R^3$ and $R^4$ each independently is hydrogen or alkyl having 1 to 6 carbon atoms; and m and n each is an integer of 1 to 10, provided that not all of substituents $R^2$, $R^3$ and $R^4$ are hydrogen.

2. An oxetane copolymer obtained by radical-polymerizing an oxetane compound represented by the following formula (1), its number average molecular weight converted to polystyrene, which is measured by GPC, being in the range of 1,000 to 1,000,000, (1)

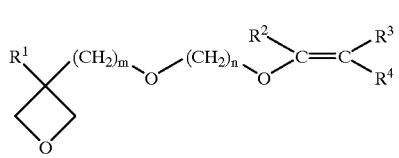

wherein substituent $R^1$ is hydrogen, alkyl, fluorine, fluoroalkyl, ally, aryl, furyl or thienyl; substituents $R^2$, $R^3$ and $R^4$ each independently is hydrogen or alkyl having 1 to 6 carbon atoms; and m and n each is an integer of 1 to 10.

3. The oxetane copolymer according to claim 2, which is represented by the following formula (2):

(2)

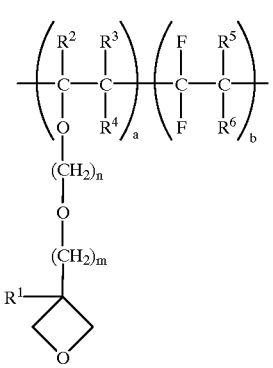

wherein substituent $R^1$ is hydrogen, alkyl, fluorine, fluoroalkyl, ally, aryl, furyl or thienyl; substituents $R^2$, $R^3$ and $R^4$ each independently is hydrogen or alkyl having 1 to 6 carbon atoms; $R^5$ is hydrogen, fluorine or chlorine; $R^6$ is hydrogen, fluorine, fluoroalkyl, alkoxy or fluorinated alkoxy; m and n each is an integer of 1 to 10; and a and b each is in the range of 0.1 to 99.9% by mole.

4. The oxetane copolymer according to claim 2, which comprises, as a monomer component, a fluorine compound represented by the following general formula (3):

(3)

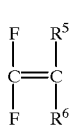

wherein substituent $R^5$ is hydrogen, fluorine or chlorine; and substituent $R^6$ is hydrogen, fluorine, fluoroalkyl, alkoxy, or fluorinated alkoxy.

5. A process for producing an oxetane compound represented by the general formula (1), by reacting an oxetane alcohol compound represented by the following formula (4)

with a halogenated vinyl ether compound represented by the following formula (5) in the presence of a phase transfer catalyst:

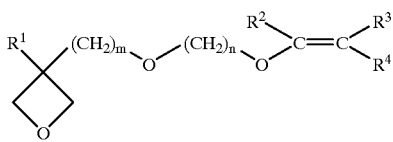
(1)

wherein substituent $R^1$ is hydrogen, alkyl, fluorine, fluoroalkyl, ally, aryl, furyl or thienyl; substituents $R^2$, $R^3$ and $R^4$ each independently is hydrogen or alkyl having 1 to 6 carbon atoms; and m and n each is an integer of 1 to 10,

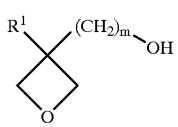
(4)

wherein substituent $R^1$ and repetition number m are the same in the formula (1),

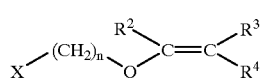
(5)

wherein substituents $R^2$, $R^3$ and $R^4$ and repetition number n each is the same in the formula (1), and X is a halogen atom.

6. The oxetane compound according to claim 1, wherein $R^1$ is $C_1$–$C_4$ alkyl.

7. The oxetane compound according to claim 6, wherein $R^1$ is methyl or ethyl.

8. The oxetane compound according to claim 1, wherein each of $R^2$, $R^3$ and $R^4$ is hydrogen.

9. The oxetane compound according to claim 1, wherein m is 1 to 4.

10. The oxetane compound according to claim 1, wherein n is 2 to 5.

11. The oxetane copolymer according to claim 4, wherein said fluorine compound represented by the formula (3) is selected from a first group fluorine compound consisting of tetrafluoroethylene, hexafluoropropylene, 3,3,3-trifluoropropylene, chlorotrifluorethylene and fluorinated vinylidene.

12. The oxetane copolymer according to claim 4, wherein said fluorine compound represented by the formula (3) is selected from a second group fluorine compound consisting of alkyl perfluorovinyl ethers, alkoxyalkyl perfluorovinyl ethers; perfluoro (alkyl vinyl ethers) and perfluoro (alkoxy alkyl vinyl ethers).

13. The oxetane copolymer according to claim 12, wherein said perfluoro (alkyl vinyl ethers) are selected from the group consisting of perfluoro (methyl vinyl ethers), perfluoro (ethyl vinyl ether), perfluoro (propyl vinyl ether) and perfluoro (isobutylvinyl ether).

14. The oxetane copolymer according to claim 12, wherein said perfluoro (alkoxyalkyl vinyl ether) is perfluoro (propoxypropyl vinyl ether).

15. The oxetane copolymer according to claim 4, which comprises from 0.1 to 2,000 parts by weight of the fluorine compound per 100 parts by weight of the oxetane compound.

16. The oxetane copolymer according to claim 2, wherein said radical-polymerizing is effected in the presence of a radical generator, which is polysiloxane compound containing an azo group.

17. The oxetane copolymer according to claim 2, which has a number average molecular weight of from 5,000 to 500,000.

18. The oxetane copolymer according to claim 2, which has a water absorption of 0.1 to 7% by weight.

19. The oxetane copolymer according to claim 2, which further contains units obtained from an unsaturated monomer having an epoxy group.

20. The oxetane copolymer according to claim 2, which further contains units obtained from an unsaturated monomer having a hydroxy group.

21. The process according to claim 5, wherein said compound of the formula (4) is selected from the group consisting of 3-methyl-3-oxetane methanol, 3-methyl-3-oxetane ethanol, 3-methyl-3-oxetane propanol, 3-ethyl-3-oxetane methanol, 3-ethyl-3-oxetane propanol, 3-propyl-3-oxetane methanol, 3-propyl-3-oxetane ethanol and 3-propyl-3-oxetane propanol.

22. The process according to claim 5, wherein said compound of the formula (5) is selected from the group consisting of 2-chloroethyl vinyl ether, 2-bromoethyl vinyl ether, 3-chloropropyl vinyl ether, 3-bromopropyl vinyl ether, 4-chlorobutyl vinyl ether and 4-bromobutyl vinyl ether.

23. The process according to claim 5, wherein 0.1 to 10 moles of the halogenated vinyl ether compound of the formula (5) is reacted with 1 mole of the oxetane alcohol compound of the formula (4).

24. The process according to claim 5, which is effected at a temperature of 0 to 100° C.

25. The process according to claim 5, which is effected at a temperature of 10 to 90° C.

26. The process according to claim 5, which is effected at a pH of from 5 to 14.

27. The process according to claim 26, which is effected at a pH of from 6 to 14.

28. The process according to claim 27, which is effected at a pH of from 7 to 14.

29. The process according to claim 5, which is effected in the presence of a phase transfer catalyst.

30. The process according to claim 29, wherein said phase transfer catalyst is selected from the group consisting of a quaternary ammonium salt and a quaternary phosphonium salt.

* * * * *